US012796974B2

(12) United States Patent
Dietiker

(10) Patent No.: US 12,796,974 B2
(45) **Date of Patent: *Nov. 17, 2026**

(54) SYSTEM AND METHOD FOR A NON-INVASIVE MEDICAL SENSOR

(71) Applicant: BIOINTELLISENSE, INC., Golden, CO (US)

(72) Inventor: Thomas Dietiker, Palos Verdes Estates, CA (US)

(73) Assignee: BIOINTELLISENSE, INC., Golden, CO (US)

( * ) Notice: Subject to any disclaimer, the term of this patent is extended or adjusted under 35 U.S.C. 154(b) by 512 days.

This patent is subject to a terminal disclaimer.

(21) Appl. No.: 17/742,106

(22) Filed: May 11, 2022

(65) Prior Publication Data

US 2022/0338766 A1 Oct. 27, 2022

Related U.S. Application Data

(63) Continuation of application No. 16/694,867, filed on Nov. 25, 2019, now Pat. No. 11,350,861, which is a (Continued)

(51) Int. Cl.
*A61B 5/1455* (2006.01)
*A61B 5/00* (2006.01)

(52) U.S. Cl.
CPC ........ *A61B 5/14551* (2013.01); *A61B 5/1455* (2013.01); *A61B 5/6826* (2013.01); (Continued)

(58) Field of Classification Search
CPC .............. A61B 5/1455; A61B 5/14551; A61B 5/14552; A61B 5/6826; A61B 5/6832; (Continued)

(56) References Cited

U.S. PATENT DOCUMENTS 3,412,729 A * 11/1968 Smith, Jr. .......... A61B 5/14552 600/324
3,638,640 A 2/1972 Shaw
(Continued)

FOREIGN PATENT DOCUMENTS

CA 3131501 8/2019
CN 101884541 A 11/2010
(Continued)

OTHER PUBLICATIONS

International Search Report and Written Opinion Dated Jan. 14, 2014 as received in application No. PCT/US2014/60004.
(Continued)

*Primary Examiner* — Eric F Winakur
(74) *Attorney, Agent, or Firm* — Maschoff Brennan

(57) ABSTRACT

A method and system for measuring oxygen levels and various blood constituents utilizing a sensor having one or more light sources, and one or more light detectors is disclosed. The system is capable of using data collected by the one or more detectors from a non-monochromatic light source to provide accurate information during motion events occurring with an extremity the sensor. The system is also capable of detecting and providing an alert if the sensor is not properly placed on a patient or becomes disengaged therefrom.

18 Claims, 21 Drawing Sheets

Related U.S. Application Data continuation of application No. 15/517,477, filed as application No. PCT/US2014/060004 on Oct. 10, 2014, now Pat. No. 10,485,463.

(52) U.S. Cl.
CPC .......... *A61B 5/6832* (2013.01); *A61B 5/6844* (2013.01); *A61B 5/7221* (2013.01); *A61B 5/14552* (2013.01); *A61B 5/6838* (2013.01); *A61B 5/7207* (2013.01); *G01N 2201/121* (2013.01)

(58) Field of Classification Search
CPC ... A61B 5/6838; A61B 5/6844; A61B 5/7207; A61B 5/7221
See application file for complete search history.

(56) References Cited

U.S. PATENT DOCUMENTS 3,799,672 A 3/1974 Vurek
3,998,550 A 12/1976 Konishi
4,603,700 A 8/1986 Nichols
4,621,643 A 11/1986 New, Jr.
4,653,498 A 3/1987 New, Jr.
4,700,708 A 10/1987 New, Jr.
4,714,080 A 12/1987 Edgar, Jr.
4,770,179 A 9/1988 New, Jr.
4,796,636 A 1/1989 Branstetter
4,824,242 A 4/1989 Frick
4,834,532 A 5/1989 Yount
4,867,557 A 9/1989 Takatani
4,869,253 A 9/1989 Craig, Jr.
4,913,150 A 4/1990 Cheung
4,942,877 A 7/1990 Sakai
5,058,588 A 10/1991 Kaestle
5,111,817 A 5/1992 Clark
5,113,861 A 5/1992 Rother
5,190,038 A 3/1993 Polson
5,216,598 A 6/1993 Branstetter
5,218,962 A 6/1993 Mannheimer
5,246,002 A 9/1993 Prosser
5,259,381 A 11/1993 Cheong
5,267,562 A 12/1993 Ukawa
5,278,627 A 1/1994 Aoyagi
5,279,295 A 1/1994 Martens
5,368,224 A 11/1994 Richardson
5,377,674 A 1/1995 Kuestner
5,398,680 A 3/1995 Polson
5,421,329 A 6/1995 Casciani
5,448,991 A 9/1995 Polson
5,490,505 A 2/1996 Diab
5,503,148 A 4/1996 Pologe
5,564,417 A 10/1996 Chance
5,632,272 A 5/1997 Diab
5,645,059 A 7/1997 Fein
5,685,299 A 11/1997 Diab
5,692,505 A 12/1997 Fouts
5,694,930 A 12/1997 Pries
5,758,644 A 6/1998 Diab
5,779,630 A 7/1998 Fein
5,782,756 A 7/1998 Mannheimer
5,807,247 A 9/1998 Merchant
5,820,550 A 10/1998 Polson
5,823,950 A 10/1998 Diab
5,827,182 A 10/1998 Raley
5,830,137 A 11/1998 Scharf
5,841,536 A 11/1998 Dimmick
5,842,981 A 12/1998 Larsen
5,921,921 A 7/1999 Potratz
5,934,277 A 8/1999 Mortz
5,987,343 A 11/1999 Kinast
5,995,858 A 11/1999 Kinast
6,011,686 A 1/2000 Grasso et al.
6,018,673 A 1/2000 Chin
6,036,642 A 3/2000 Diab
6,041,247 A 3/2000 Weckstrom
6,044,283 A 3/2000 Fein
6,081,735 A 6/2000 Diab
6,115,621 A 9/2000 Chin
6,163,715 A 12/2000 Larsen
6,181,959 B1 1/2001 Schollermann
6,206,830 B1 3/2001 Diab
6,215,295 B1 4/2001 Smith
6,226,540 B1 5/2001 Bemreuter
6,230,035 B1 5/2001 Aoyagi
6,253,097 B1 6/2001 Aronow
6,263,222 B1 7/2001 Diab et al.
6,272,363 B1 8/2001 Casciani
6,356,774 B1 3/2002 Bernstein
6,501,974 B2 12/2002 Huiku
6,537,225 B1 3/2003 Mills
6,600,940 B1 7/2003 Fein
6,611,320 B1 8/2003 Lindberg
6,628,975 B1 9/2003 Fein
6,667,803 B1 12/2003 Flessland
6,673,596 B1 1/2004 Sayler
6,741,876 B1 5/2004 Scecina
6,889,153 B2 5/2005 Dietiker
7,124,048 B2 10/2006 Dietiker
8,271,063 B2 * 9/2012 Dietiker ............. A61B 5/14551 600/322
10,485,463 B2 11/2019 Dietiker
10,940,340 B2 3/2021 Turcotte
2001/0005773 A1 6/2001 Larsen
2001/0020123 A1 9/2001 Diab
2001/0029326 A1 10/2001 Diab
2001/0037059 A1 11/2001 Stone
2002/0082488 A1 6/2002 Al-Ali
2002/0161287 A1 10/2002 Schmitt
2008/0281174 A1 11/2008 Dietiker
2010/0081944 A1 4/2010 Baker, Jr.
2010/0130840 A1 5/2010 Isaacson
2010/0331636 A1 12/2010 Hubner
2011/0112388 A1 * 5/2011 Kuech ................ A61B 5/14546 600/341
2012/0184832 A1 7/2012 Diab
2013/0018241 A1 1/2013 Bezzerides
2014/0073944 A1 3/2014 Rodriguez-Llorente
2014/0275882 A1 9/2014 Addison
2017/0020443 A1 1/2017 Fein
2017/0311855 A1 11/2017 Dietiker
2018/0014793 A1 1/2018 Bejo-Huerto
2019/0261859 A1 8/2019 Dietiker

FOREIGN PATENT DOCUMENTS

CN 102499694 A 6/2012
CN 104019908 A 9/2014
CN 104068865 A 10/2014
EP 1437087 A1 7/2004
WO 2002014793 A3 2/2002
WO 2016057042 A1 4/2016
WO 2017009233 A1 1/2017
WO 2017053925 A1 3/2017
WO 2019164676 A1 8/2019

OTHER PUBLICATIONS

International Search Report and Written Opinion Dated May 9, 2019 as received in application No. PCT/US2019/17107.
International Preliminary Report dated Apr. 20, 2017 as received in application No. PCT/US2014/60004.
Sources for Illumination dowloaded from https://www.spiedigitallibrary.org/ebooks, Dec. 7, 2018.
Mendelson, "Pulse Oximetry" Worcester Polytechnic Institute, 2006.
Chinese Office Action dated May 28, 2019 as received in application No. 2014800837461.
European Search Report dated Apr. 24, 2018 as received in application No. 14903626.1.
European Search Report dated Nov. 27, 2009 as received in application No. 07809605.

(56) References Cited

OTHER PUBLICATIONS

International Search Report Dated Feb. 27, 2009 as received in application No. PCT/US2001/25109.
International Preliminary Report dated Sep. 3, 2020 as received in application No. PCT/US2019/17107.
European Communication Pursuant to Rules 161(1) and 162 EPC dated Oct. 9, 2020 as received in application No. 19710824.4.
International Search Report and Written Opinion Dated Jan. 14, 2015 as received in application No. PCT/US2014/60004.

* cited by examiner

| 50% | 50% |
|---|---|
| WHITE SPO2 LOOKUP TABLE | VAR SLOPE |
| 87 | 81.24750363 |
| 88 | 81.56750363 |
| 89 | 81.88750363 |
| 90 | 82.20750363 |
| 91 | 82.52750363 |
| 92 | 82.84750363 |
| 93 | 83.16750363 |
| 94 | 83.48750363 |
| 95 | 83.80750363 |
| 96 | 84.12750363 |
| 97 | 84.44750363 |
| 98 | 84.76750363 |
| 99 | 85.08750363 |

SYSTEM AND METHOD FOR A NON-INVASIVE MEDICAL SENSOR

RELATED APPLICATIONS

This application is a continuation of U.S. application Ser. No. 16/694,867, filed Nov. 25, 2019, which is a continuation application of U.S. patent application Ser. No. 15/517,477 filed Apr. 6, 2017 by Thomas Dietiker and titled, "System and Method for a Non-Invasive Medical Sensor", which is a national stage entry, under 35 USC § 371, of PCT/US14/60004, filed Oct. 10, 2014 by Thomas Dietiker and titled, "System and Method for a Non-Invasive Medical Sensor". The contents of these applications are incorporated herein by reference in their entirety.

FIELD OF THE INVENTION

The present invention relates generally to non-invasive medical sensing devices, and in particular to error correction for a medical sensor.

FEDERALLY SPONSORED RESEARCH OR DEVELOPMENT

None.

DESCRIPTION OF RELATED ART

Monochromatic tight sources are utilized in a broad range of applications in many distinct fields of technology including the consumer, industrial, medical, defense and scientific fields. In the medical field an emitter-receiver pair of monochromatic light sources in form of light-emitting diodes (LEDs) or similar devices are often utilized in medical sensing devices to obtain accurate non-invasive measurements. An example application of such a medical sensing device may include a blood constituent monitoring system and/or a non-invasive oximeter that may be utilized to monitor arterial oxygen saturation.

In non-invasive oximetry, monochromatic light having a known specific wavelength is typically transmitted from an emitter LED through a target, such as biological tissue carrying blood, to a photodetector. The photodetector receives and measures a portion of transmitted coherent light that is neither absorbed nor reflected from the blood in the biological tissue in order to determine the oxygen saturation (SPO2) within the blood Similarly, an example of an industrial application may include a non-invasive sensor system having a monochromatic light of a known specific wavelength transmitted from a coherent light source (such as an LED emitter) through a target, such as a fluid or material, to a photodetector.

Unfortunately, these types of non-invasive sensor systems utilizing a monochromatic light source require accurate prior knowledge of the wavelength of the monochromatic light source in order to determine the amount of monochromatic light that is absorbed or reflected through the target, One way of having the prior knowledge of the wavelength is to select monochromatic light source emitters that have wavelengths within a certain range of tolerance. As such, attempts at determining the wavelength have included a binning process of selecting LEDs within the required nominal wavelength specifications and/or encoding data corresponding to the wavelength employed in a sensor as part of the sensor by means of a resistor, memory device or similar component.

However, it is appreciated by those skilled in the art and familiar with the production of emitter-photodiode sensing devices that there is a need to be able to select from a wider variation of emitter output wavelengths in reducing the production costs and defect rates of the sensing devices. As an example, typical production techniques require selection of an emitter within 2 nm of a target wavelength, which may lead to rejection of 40-60% of the component emitters. Moreover, an additional problem is that a selected emitter, which was within the target wavelength at time of production, will typically degrade over time, vary with temperature and drive current, and further the drive circuit may become unstable and cause a wavelength shift. Attempts to solve the wavelength problem have included systems that correlate the wavelength shift to a change in drive circuit current. The change in drive circuit current drives the LED to a specific wavelength. Typically, these systems include a scheme for determining the wavelength shift of the photodiodes via a series of filters, diffusers and a plurality of photodetectors. Unfortunately, this approach is too complex and expensive for practical manufacturing techniques and cannot be employed in each sensor being used with monitoring devices.

There is also a significant need to be able to reduce or eliminate variations resulting from patient movement, also commonly referred to as 'Motion Artefacts', differences in skin pigmentation and to detect fault situations, like for example, when a sensor becomes disengaged from a patient and is no longer able to deliver accurate information. Using current sensors and monitoring systems, such situations are generally difficult to detect and can lead to false readings and risk to the patient.

Therefore, there is a need for a non-invasive sensor system that is capable of measuring the wavelength of a light source without requiring prior knowledge of the wavelength of the light source and is not complex or expensive to manufacture. Moreover, there is a need for error reduction is such sensor systems.

There is also a need for a non-invasive sensor system which is capable of providing reliable data during motion events, or when the subject is engaged movement or other physical activity or to provide a satisfactory notification or warning resulting from a patient disengaging the non-invasive sensor.

SUMMARY OF THE INVENTION

The present invention is directed to a non-invasive medical sensing device and system capable of providing correct data in response to a patients movement and providing an alert should the device become disengage from the patient.

According to one aspect of the invention the sensor has one or more light sources and one or more light detectors. At least one of the detectors produces an output in response to the received light. Further, electrical circuitry responsive to the output generates a pulse waveform proportional to the arterial and venous pulse of a human body, wherein the pulse waveform is used to synchronize an arterial-pulse measurement of the absorption or reflectance of one or more monochromatic or non-monochromatic light sources.

According to one aspect of the invention, a method is provided.

The method includes providing a first detector and second detector in a non-invasive optical sensor and emitting light from a non-monochromatic light source in the non-invasive optical sensor periodically. A first signal from the first detector and a second signal from the second detector are generated, resulting from light periodically emitted by the non-monochromatic light source sampled by the first detector and the second detector, both detectors having well defined and differing spectral responses. A third signal is generated using a ratio of first signal and the second signal to determine an average spectral absorption and any changes in spectral absorption generated by the occurrence of an arterial pulse and base line spectral absorption of tissue located within the non-invasive optical sensor. According to another aspect of the invention, at least one light emitter emitting red light and at least one tight emitter emitting infrared light is provided in the non-invasive optical sensor. A red light signal level from emitted red light received by the first detector and the second detector may be generated and infrared signal level received from emitted infrared light received by the first detector and the second detector may be generated. A ratio of the red light signal level to the infrared signal level may be correlated to a corresponding value sampled at an arterial peak while the non-monochromatic light source is emitting light in order to generate oxygen saturation data in the tissue.

Oxygen saturation data may be generated using the first signal and the second signal if a motion event occurs with the tissue located within the non-invasive optical sensor.

According to another aspect of the invention, a ratio of non-monochromatic light received by the first detector and the second detector may be measured. If the ratio of received non-monochromatic light is above or below a threshold, a notification may be generated.

According to another aspect of the invention, a centroid wavelength of emitted red light may be measured. If the measured centroid wavelength is determined to be outside an acceptable centroid range, and alert may be generated. According to another aspect of the invention, the first detector and second detector may have different spectral response curves, and. The different spectral response curves may be utilized to derive a fourth signal proportional to the centroid wavelength of emitted red light.

According to another aspect of the invention, a first detector and second detector are provided in a non-invasive optical sensor. Light may be emitted from a non-monochromatic light source in the non-invasive optical sensor periodically, and an amplitude of non-monochromatic light received by the first detector and the second detector may be measured. A notification may be generated if the amplitude of received non-monochromatic light is above or below a threshold.

Other embodiments, systems, methods, features, and advantages of the present invention will be, or become, apparent to one having ordinary skill in the art upon examination of the following drawings and detailed description. It is intended that all such additional systems, methods, features, and advantages included within this description be within the scope of the present invention and be protected by the accompanying claims.

BRIEF DESCRIPTION OF THE DRAWINGS

The invention may be better understood with reference to the following figures. The components in the figures are not necessarily to scale, emphasis instead being placed upon clearly illustrating the principles of the invention. Moreover, in the figures, like reference numerals designate corresponding parts throughout the several views.

DESCRIPTION OF PREFERRED EMBODIMENTS

The following descriptions of detailed embodiments are for exemplifying the principles and advantages of the inventions claimed herein. They are not to be taken in any way as limitations on the scope of the inventions.

Figure 1:
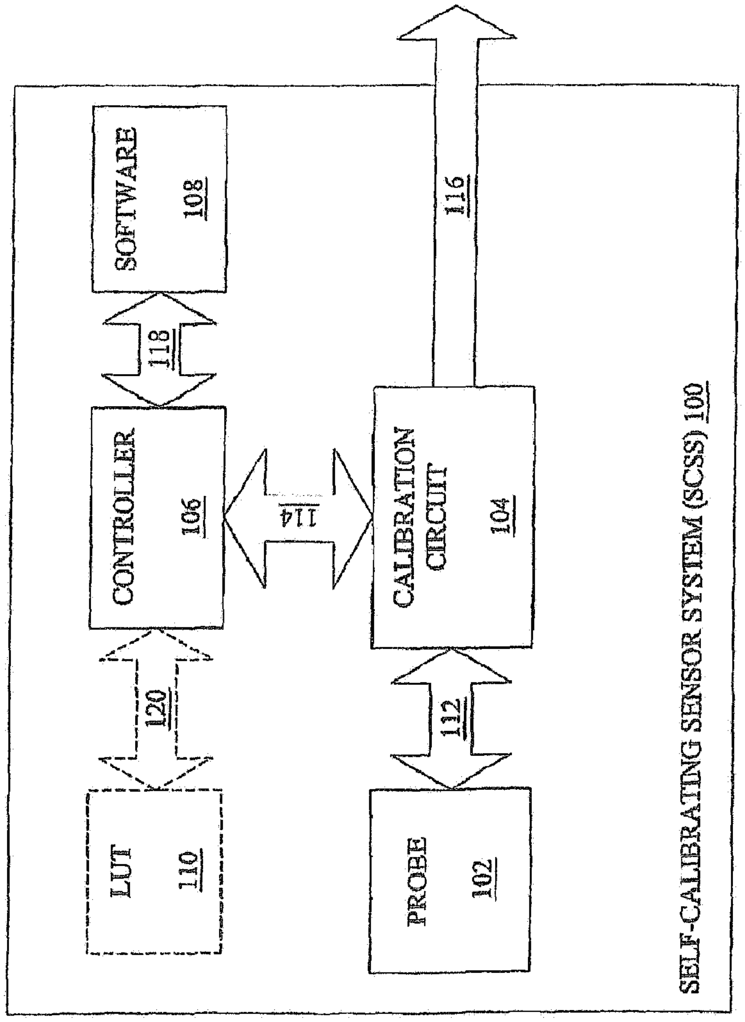
FIG. 1 illustrates a block diagram of an example implementation of a self-calibrating sensor system (SCSS)

FIG. 1 illustrates a block diagram of a self-calibrating sensor system (SCSS) 100. The SCSS 100 may include a probe 102, a calibration circuit 104, a controller 106, software 108 located in memory (not shown) and optional lookup table ("LUT") 110, The probe 102 is in signal communication, via signal path 112, to the calibration circuit 104, The calibration circuit 104 may be a divider and/or comparator circuit.

The calibration circuit 104 is in signal communication to the controller 106 and an external output device (not shown) via signal paths 114 and 116 respectively. The controller 106 is in signal communication to software 108 and optional LUT 110 via, signal paths 118 and 120, respectively.

The controller 106 may be any general-purpose processor such as an Intel XXX86, Motorola 68XXX or PowerPC, DEC Alpha or other equivalent processor. Alternatively, a specific circuit or oriented device may selectively be utilized as the controller 106. Additionally, the controller 106 may also be integrated into a signal semiconductor chip such as an Application Specific Integrated Chip (ASIC) or Reduced Instruction Set Computer (RISC), or may be implemented via a Digital Signal Processor (DSP) chip. Examples of a specific circuit or oriented device for the controller 106 may also be a mixed sionac ASIC.

The software 108 may be resident in memory (not shown) located either internally or externally to the controller 106. The software 108 includes both logic enabling the controller 106 to operate and also for self-calibrating SCSS 100.

An example of the external output device may be an oximeter such as a NPB40 manufactured by Nellcor of Pleasanton, Calif., a 9840 Series pulse oximeter manufactured Nonin Medical, Inc. of Plymouth, Minn., or an equivalent device.

Figure 2:
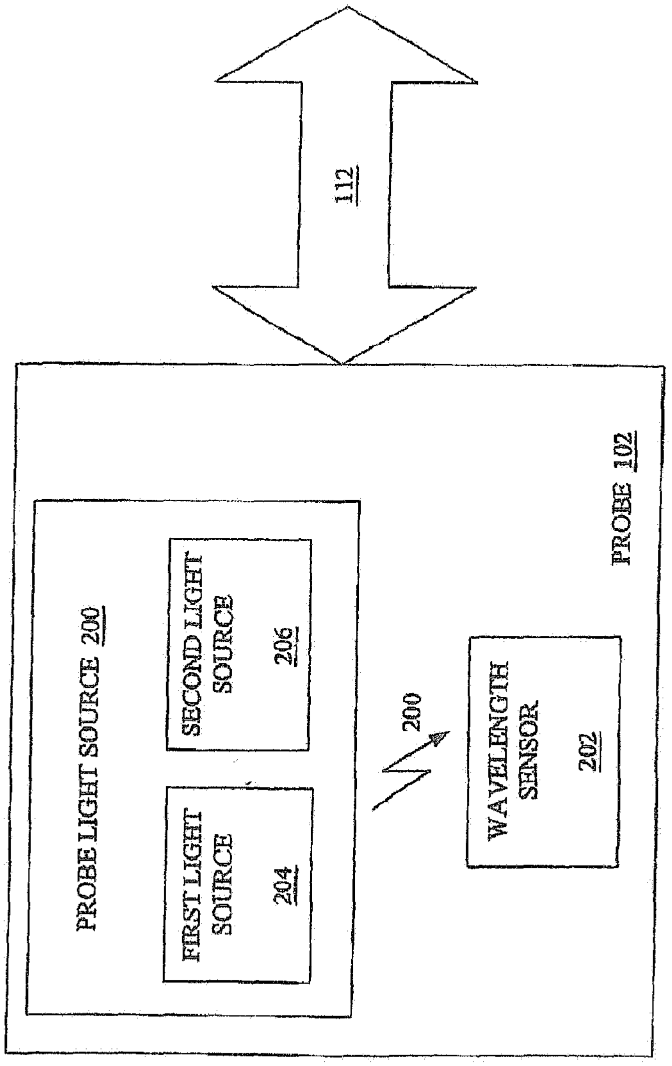
FIG. 2 illustrates a block diagram of an example implementation of the probe block of the SCSS shown FIG. 1.

FIG. 2 shows an example implementation of probe 102, Probe 102 may include a probe light source 200 and wavelength sensor 202. Probe Light source 200 may include a first light source 204 and second light source 206. First light source 204 and second light source 206 may be implemented utilizing light-emitting diodes (LEDs). As an example implementation in oximeter application, first light source 204 may be an LED emitting light radiation at a wavelength of approximately 660 nm and second light source 206 may be an LED emitting light radiation at a wavelength of approximately 880 nm Wavelength sensor 202 may be implemented utilizing a double diffusion photodiode. It is appreciated by those of skill in the art that probe light source 200 may also include multiple light sources in the order of three or more.

Figure 3:
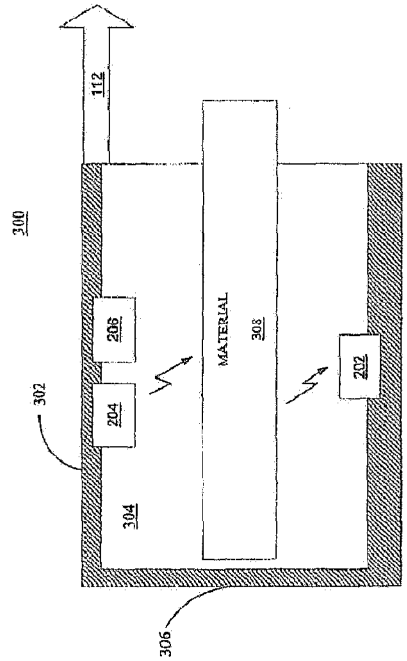
FIG. 3 illustrates a cross-sectional view of example implementation of the probe shown in FIG. 2.

In FIG. 3, a cross-sectional view of an example implementation of the probe 300 is shown. In this example, probe 300 may be a medical device such as a transmissive blood oxygen saturation and pulse rate sensor. However, it would be appreciated by one skilled in the art that probe 300 may also be a reflective sensor. Additionally, probe 300 may also be utilized for measuring other blood constituents including, but not limited to, oxyhemoglobin, bilirubin, carboxy-hemoglobin, and glucose. Probe 300 may include a rigid casing 302 having a cavity 304 and casing butt 306, first light source 204, second light source 206 and wavelength sensor 202. Probe 300 is connected to calibration circuit 104, FIG. 1, via signal path 112. A material 308, FIG. 3, such as a finger may inserted into the cavity 304.

As an example, first light source 204 and second light source 206 may be two LED emitters that produce light radiation at a wavelength of approximately 660 nm and 880 nm, respectively. Wavelength sensor 202 is supported within the rigid casing 302 opposite first light source 204 and second light source 206. First light source 204 and second light source 206 and wavelength sensor 202 may be in signal communication with a control cable (not shown). The control cable is in signal communication with an oximeter (not shown) via signal path 112. The oximeter determines the oxygen saturation of the blood in the material 308 (in this example a finger) by measuring and processing the amount of incident tight radiation reaching wavelength sensor 202 from a pulse of light radiation from first light source 204.

In operation, the SCSS 100, FIG. 1, performs a self-calibration procedure prior to and while measuring any of the properties of the material 308, FIG. 3. This self-calibration procedure includes emitting a pulse of light radiation from first light source 204 that is received as incident light radiation by wavelength sensor 202 prior to inserting material 308 into the cavity 304. The oximeter utilizes the measured incident light radiation received by wavelength sensor 202 to determine the operating wavelength of the first light source 204. Once the operating wavelength of the first light source 203 is known, the SCSS 100, FIG. 1, is utilized in combination with the oximeter to accurately determine blood oxygen saturation of the material 308.

The continuous self-calibration procedure is beneficial because it is appreciated by those skilled in the art that light radiation output by first light source 204 of 660 nm in this example implementation is in the red spectral region. It is the absorption of this red light radiation that the oximeter utilizes to determine the oxygen saturation of the blood. As such, a relatively small variation in operating wavelength may results in inaccurate readings at the oximeter. As an example, without the self-calibration procedure, if the light radiation output by first light source 204 varied in excess of .+-.2 nm from an operating wavelength required by the oximeter, the results would be inaccurate.

Figure 4A:
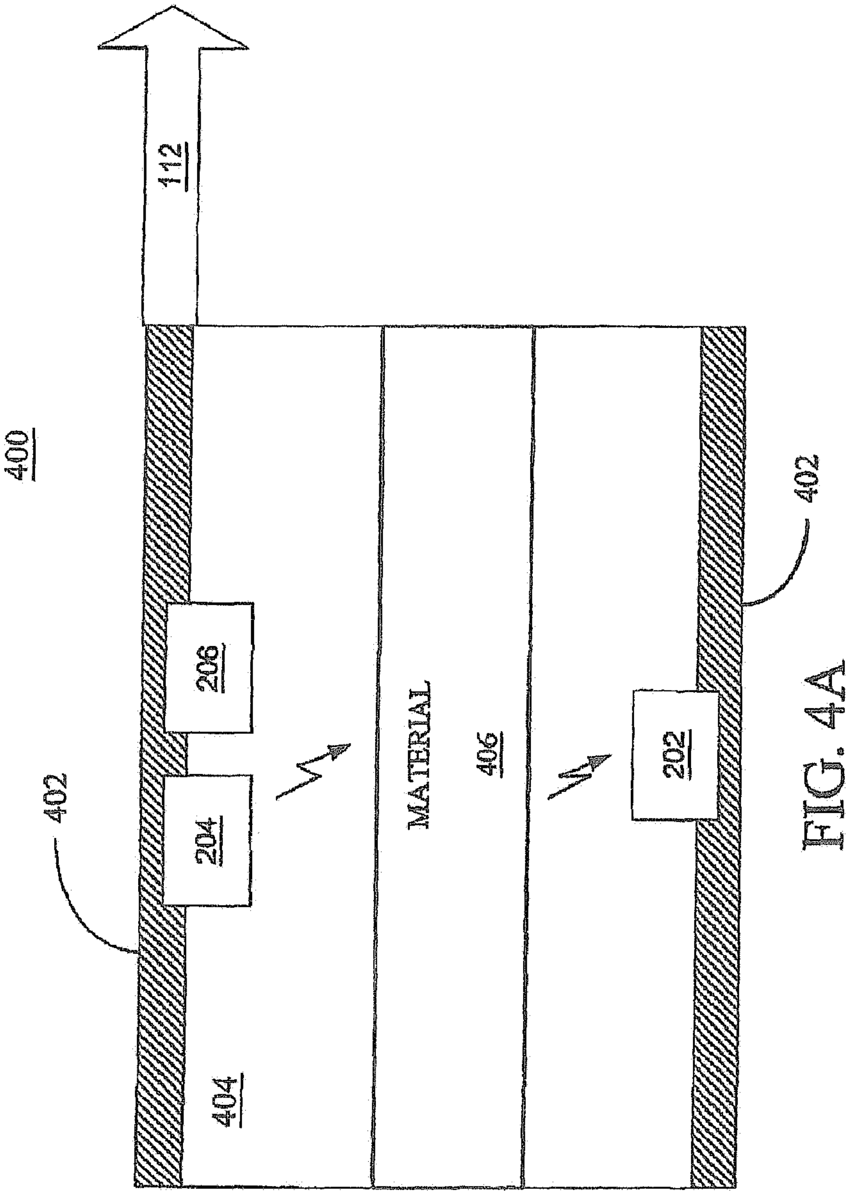
FIG. 4A illustrates a cross-sectional view of another example implementation of the probe shown in FIG. 2.

FIG. 4A illustrates a cross-sectional view of another example implementation of probe 400. In this example, probe 400 may include a rigid or flexible casing 402 having a cavity 404, first light source 204, second light source 206 and wavelength sensor 202. Similar to the previous example implementation, probe 400 is connected to calibration circuit 104, FIG. 1, via signal path 112, however, probe 400, FIG. 4A, does not have a cavity butt. A material 406 may be inserted into the cavity 404.

Similar to the previous example, first light source 204 and second light source 206 may be two LED emitters that produce light radiation at different wavelengths. Wavelength sensor 202 is supported within the rigid casing 402 opposite first light source 204 and second light source 206. First light source 204 and second light source 206 and wavelength sensor 202 may be in signal communication with a control cable (not shown). The control cable is in signal communication with a measuring device (not shown) via signal path 112. The measuring device determines the properties in the material 406 by measuring and processing the amount of incident light radiation reaching wavelength sensor 202 from a pulse of light radiation from first light source 204.

As an industrial example, the material 406 may be a fluid, liquid or solid material that exhibits optical transmissive characteristics that may be measured and utilized to determine the properties of the material. An example implementation would include measuring the properties of the material for process or quality control purposes.

Again in operation, the SCSS 100, FIG. 1, performs a self-calibration procedure prior to measuring any of the properties of the material 406, FIG. 4A. This self-calibration procedure includes emitting a pulse of light radiation from the first light source 204 that is received as incident light radiation by wavelength sensor 202 prior to inserting material 406 into the cavity 404. The measuring device utilizes the measured incident light radiation received by wavelength sensor 202 to determine the operating wavelength of the first light source 204. Once the operating wavelength of the first light source 204 is known, the SCSS 100, FIG. 1, is utilized in combination with the measuring device to accurately determine the properties of the material 406.

Figure 4B:
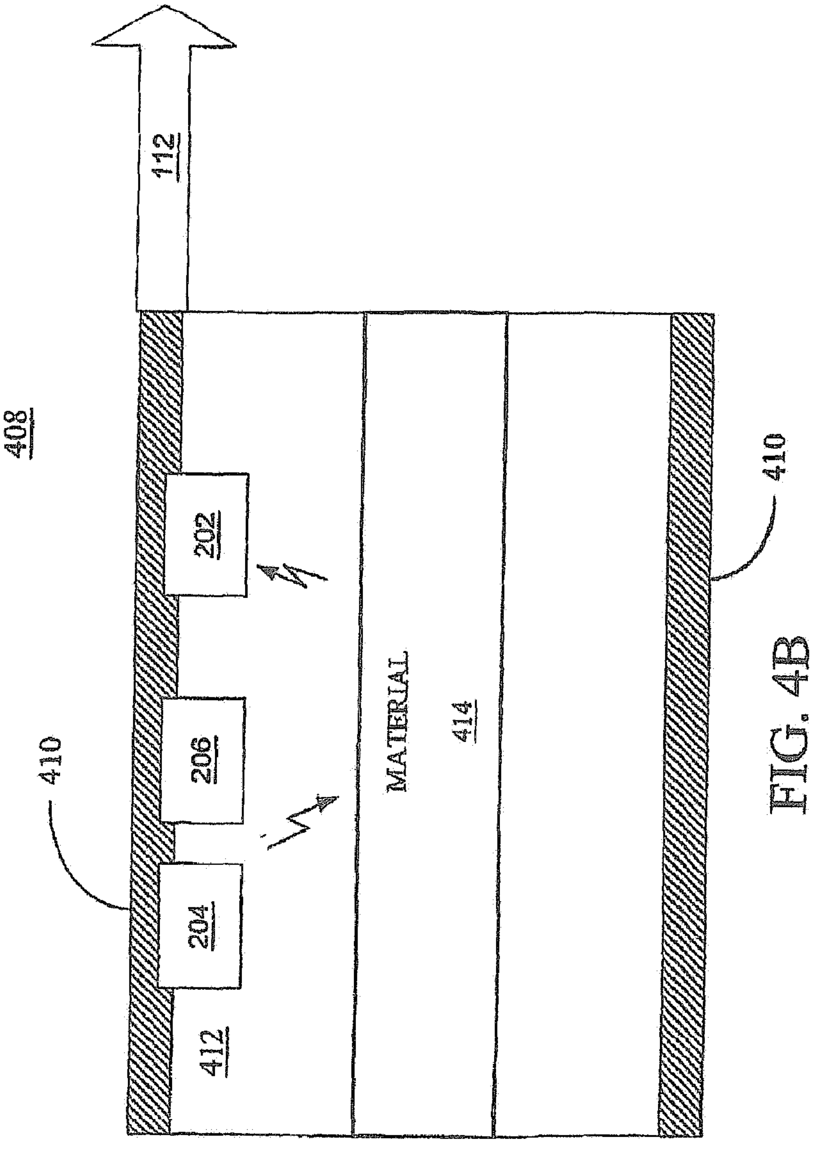
FIG. 4B illustrates a cross-sectional view of example reflective implementation of the probe shown in FIG. 2.

FIG. 4B illustrates a cross-sectional view of an example reflective implementation of probe 408. In this example, probe 408 may include a rigid or flexible casing 410 having a cavity 412, first light source 204, second light source 206 and wavelength sensor 202. Similar to the previous example implementation, probe 408 is connected to calibration circuit 104, FIG. 1, via signal path 112, however, probe 408, FIG. 4B, does not have a cavity butt. A material 414 may be inserted into the cavity 412.

Similar to the previous example, first light source 204 and second light source 206 may be two LED emitters that produce light radiation at different wavelengths. However, in this example, wavelength sensor 202 is supported within the rigid casing 410 adjacent to first light source 204 and second light source 206, First light source 204 and second light source 206 and wavelength sensor 202 may be in signal communication with a control cable (not shown). The control cable is in signal communication with a measuring device (not shown) via signal path 112. The measuring device determines the properties in the material 412 by measuring and processing the amount of incident light radiation reflected by material 412 and reaching wavelength sensor 202 from a pulse of light radiation from first light source 204.

Again, as an industrial example, the material 412 may be a fluid, liquid or solid material that exhibits optical transmissive characteristics that may be measured and utilized to determine the properties of the material. An example implementation would include measuring the properties of the material for process or quality control purposes.

Again in operation, the SCSS 100, FIG. 1, performs a self calibration procedure prior to measuring any of the properties of the material 412, FIG. 4B. This self-calibration procedure includes emitting a pulse of light radiation from the first light source 204 that is reflected by flexible casing 410 and later received as incident light radiation wavelength sensor 202 prior to inserting material 412 into the cavity 410. The measuring device utilizes the measured incident light radiation received by wavelength sensor 202 to determine the operating wavelength of the first light source 204. Once the operating wavelength of the first light source 204 is known, the SCSS 100, FIG. 1, is utilized in combination with the measuring device to accurately determine the properties of the material 412.

It is appreciated by of skill in the art that it is possible to generate signals from the wavelength sensor 202, FIG. 2 during operation of the light sources 204 and 206 through the medium (i.e., material 308, FIG. 3, 406. FIG. 4A, and/or 414, FIG. 4B) being inspected. It is also possible to generate the same signals using light reflected off the medium. Therefore, it is not necessary to couple the light sources 204, FIGS. 2 and 206 directly to the wavelength sensor 202 as long as the medium either transmits or reflects enough light to generate processable signals from the wavelength sensor 202.

Figure 5:
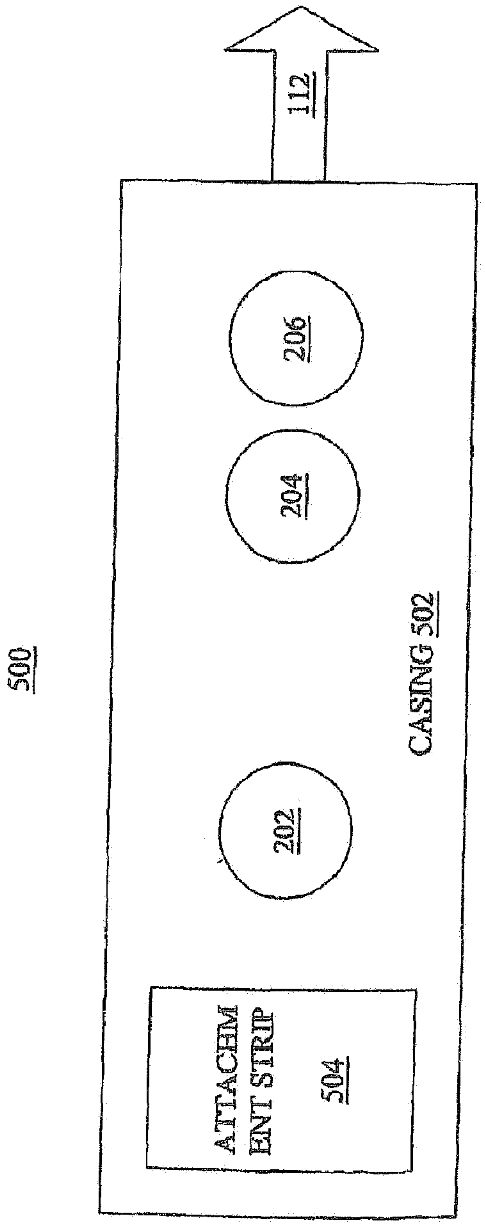
FIG. 5 is a top view of an example implementation of the probe shown in FIG. 4.

In FIG. 5, a top view of an example medical implementation of probe 500 having a flexible casing (i.e., flexible strip) 502 is shown. Probe 500 may include first light source 204, second light source 206 and wavelength sensor 202. In this example implementation, probe 500 is a blood oxygen saturation and pulse rate sensor that utilizes the flexible strip 502 to attach to a material, such as a body part (not shown). The probe 500 is connected to an oximeter (not shown) via signal path 112. The flexible strip 502 may be wrapped around the body part and affixed to itself via an attachment strip (such as an adhesive strip) 504. Example body parts would include a finger, toe, ear-lobe, arm, leg or other similar parts.

As an example, first light source 204 and second light source 206 may be two LED emitters that produce light radiation at a wavelength of approximately 660 nm and 880 nm, respectively. Wavelength sensor 202 is supported within the flexible strip 502 and placed opposite first light source 204 and second light source 206 when the flexible strip 502 is wrapped around a body part. First light source 204 and second light source 206 and wavelength sensor 202 may be in signal communication with a control cable (not shown). The control cable is in signal communication with an oximeter (not shown) via signal path 112. The oximeter determines the oxygen saturation of the blood in the body part by measuring and processing the amount of incident light radiation reaching wavelength sensor 202 from a pulse of light radiation from first light source 204.

Figure 6:
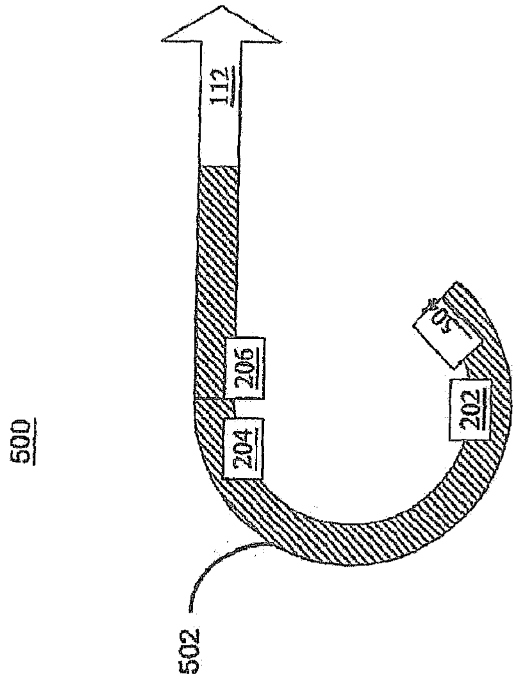
FIG. 6 is a cross-sectional view of the probe implementation of FIG. 5.

As before, in operation, the SCSS 100, FIG. 1, performs a self-calibration procedure prior to measuring any of the properties of the body part. This self-calibration procedure includes, prior to wrapping flexible strip 502 around the body part, bending the flexible strip 502 so that the first light source 204 and second light source 206 are opposite in special orientation to wavelength sensor 202 and then emitting a pulse of tight radiation from the first light source 204 that is received as incident tight radiation by wavelength sensor 202. The oximeter utilizes the measured incident light radiation received by wavelength sensor 202 to determine the operating wavelength of the first light source 204. Once the operating wavelength of the first light source 204 is known, placed around a body part and the wavelength sensor 202 measures the incident light radiation emitted by the first light source 204 and passing through the blood flowing within the body part. The SCSS 100, FIG. 1, is then utilized in combination with the oximeter to accurately determine blood oxygen saturation of the body part. In FIG. 6, a cross-sectional view of the probe 500 is shown in a wrap type position.

Figure 7:
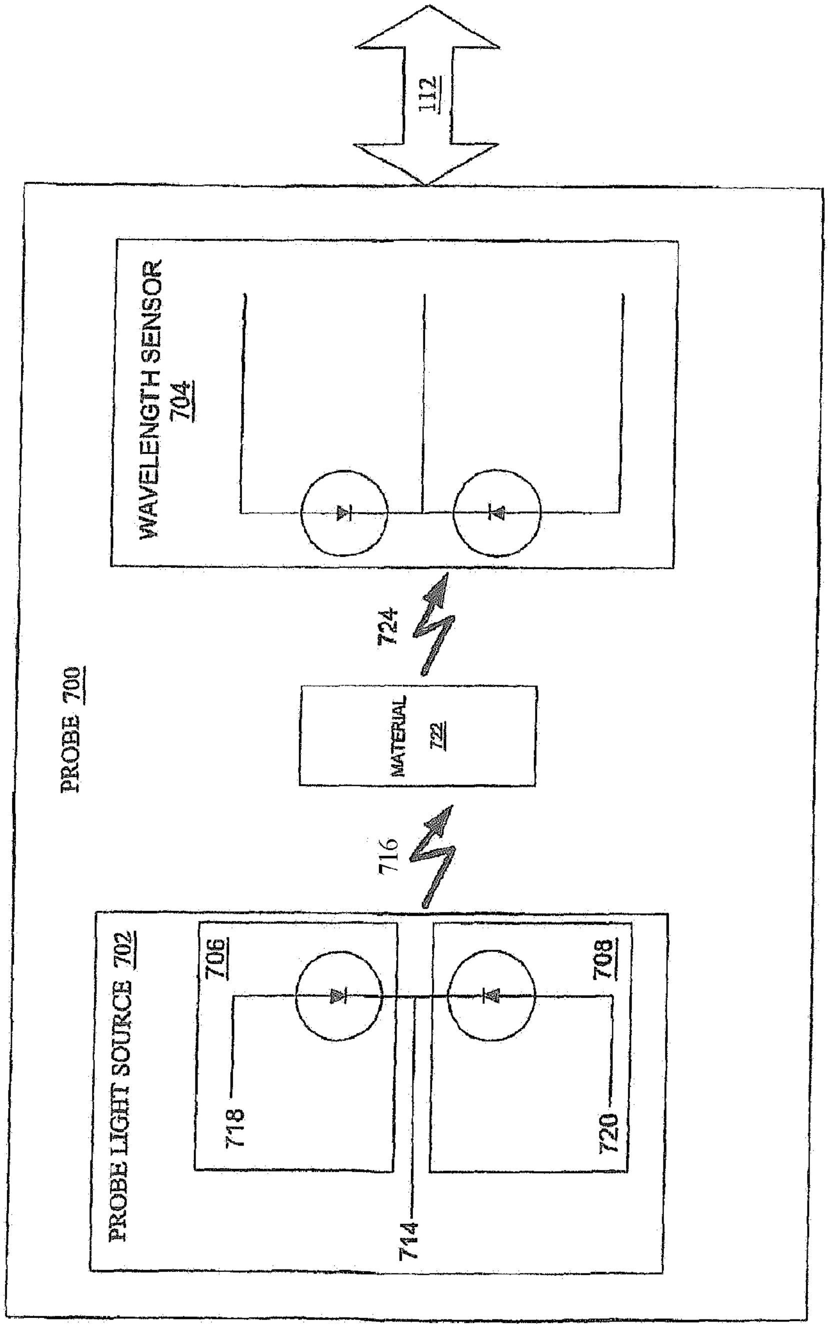
FIG. 7 illustrates an example implementation of the probe block shown in FIG. 2 utilizing photodiodes.

In FIG. 7, an example implementation of the probe 700 is shown utilizing photodiodes. Similar to FIG. 2, Probe 700, FIG. 7, includes probe light source 702 and wavelength sensor 704. Probe light source 702 includes first light source 706 and second light source 708. First light source 706 may include LED 710 and second light source may include LED 712. Wavelength sensor 704 is a double diffusion photodiode.

As an example of operation, LED 710 and LED 712 may have their cathodes grounded in common at signal path 714 and may emit light radiation 716 at wavelengths 660 nm and 880 nm, respectively, when a voltage is applied at anodes 718 and 720, respectively. The emitted light radiation 716 is incident on material 722. A part of the emitted light radiation 716 is transmitted through material 722 and is received as incident light radiation 724 by wavelength sensor 704. As before, in order to properly measure the properties of the material 722 from the received incident light radiation 724, the SCSS 100, FIG. 1 performs a self-calibration procedure.

The SCSS 100, FIG. 1, performs a self-calibration procedure prior to measuring any of the properties of the material 722. This self-calibration procedure includes emitting a pulse of light radiation 716 from LED 710 that is received as incident light radiation 724 by wavelength sensor 704 prior to inserting material 722 between the probe light source 702 wavelength sensor 704. The oximeter utilizes the measured incident light radiation 724 received by wavelength sensor 704 to determine the operating wavelength of LED 710. Once the operating wavelength of LED 710 is known, the SCSS 100, FIG. 1, is utilized in combination with the oximeter to accurately determine blood oxygen saturation of the material 722.

Figure 8:
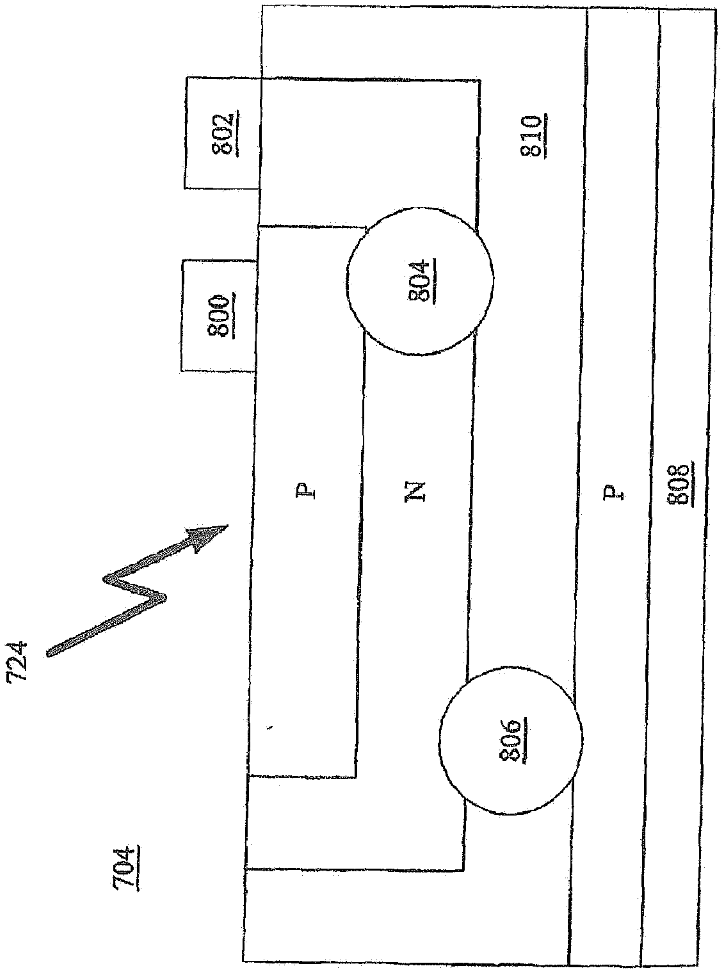
FIG. 8 illustrates a cross-sectional view of an example implementation of the wavelength sensor block shown in FIG. 7 utilizing a double diffusion photodiode.

FIG. 8 illustrates a cross-sectional view of the wavelength sensor 704 receiving incident light radiation 724 utilizing a double diffusion photodiode (also known as a double junction photodiode). Photodiodes with double diffusion are typically utilized to accurately measure the centroid wavelength of light sources such as LEDs 710 and 712. Double diffusion photodiodes are processed with two junctions, one on the top surface and one on the back surface of a semiconductor photodiode (such as a Si-photodiode), each junction typically exhibits a different and well-defined spectral response. As result, by measuring the quotient of signals generated by the two junctions, the centroid wavelength of any given monochromatic light source may be determined.

The wavelength sensor 704 has two p-n junctions constructed vertically on a common silicon substrate. The wavelength sensor 704 includes a first anode 800, common cathode 802, first diode 804 (also known as an upper diode), second diode 806 (also known as a lower diode), second anode 808, and a thin active region 810. The first anode 800 is positioned on the top surface above the common cathode 802 forming the first diode 804. The thickness of the first diode 804 is chosen so that the energy of the shortest wavelength being measured from the incident light radiation 724 is absorbed entirely therein. The second diode 806 is formed between the common cathode 802 and the second anode 808 that placed on the bottom surface with the thin active region 810 between the common cathode 802 and the second anode 808. The thickness of the thin active region 810 is selected to allow for absorption of substantially all of the longest measured wavelength incident light radiation 724.

Figure 9:
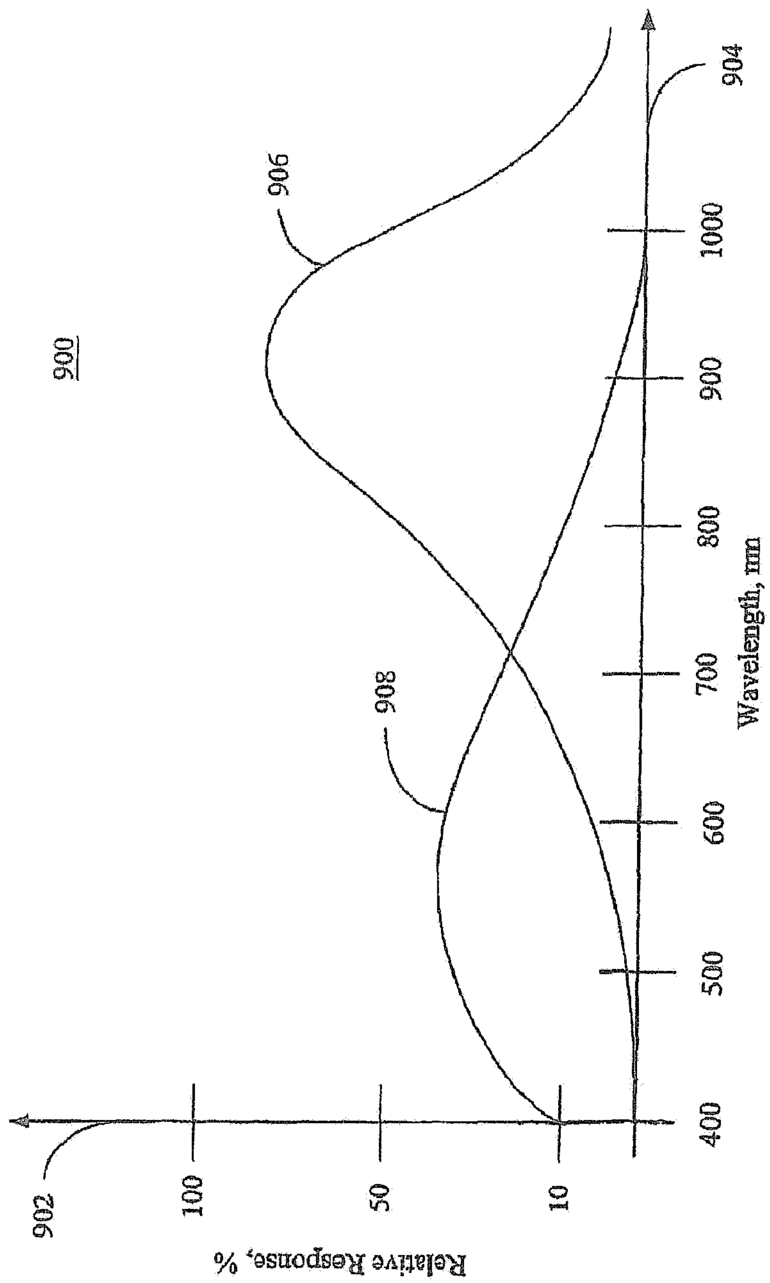
FIG. 9 is a graph of the response curve of the wavelength sensor shown in FIG. 8.

FIG. 9 illustrates a typical plot 900 of the spectral response of the wavelength sensor 704, FIG. 8. The plot 900, FIG. 9, has a vertical axis 902 representing relative response, in percentage, of the wavelength sensor 704, FIG. 8, and a horizontal axis 904, FIG. 9, representing the wavelength of the incident light radiation 724, FIG. 8. The plot 900, FIG. 9, shows two response curves 906 and 908 representing the relative response versus wavelength for the first diode 804, FIG. 8, and the second diode 806, respectively.

As an example of operation of the wavelength sensor 704 the first diode 804 may have an enhanced blue response and the second diode 806 may have an enhanced red response. In this example, the absorbed radiation of the incident light radiation 724 between the red and blue responses (such as between 450 and 900 nm) generates two photocurrent signals proportional to the wavelength of the incident light radiation 724. The quotient of these photocurrent signals is independent of the light level up to saturation point of the wavelength sensor 704. Utilizing this example, the wavelength of either monochromatic incident light radiation 724 or the spectral density peak of polychromatic incident light radiation 724 may be determined. An example of the wavelength sensor 704 may be a PSS WS-7.56 wavelength sensor produced by Pacific Silicon Sensor, Inc. of Westlake Village, Calif.

Figure 10:
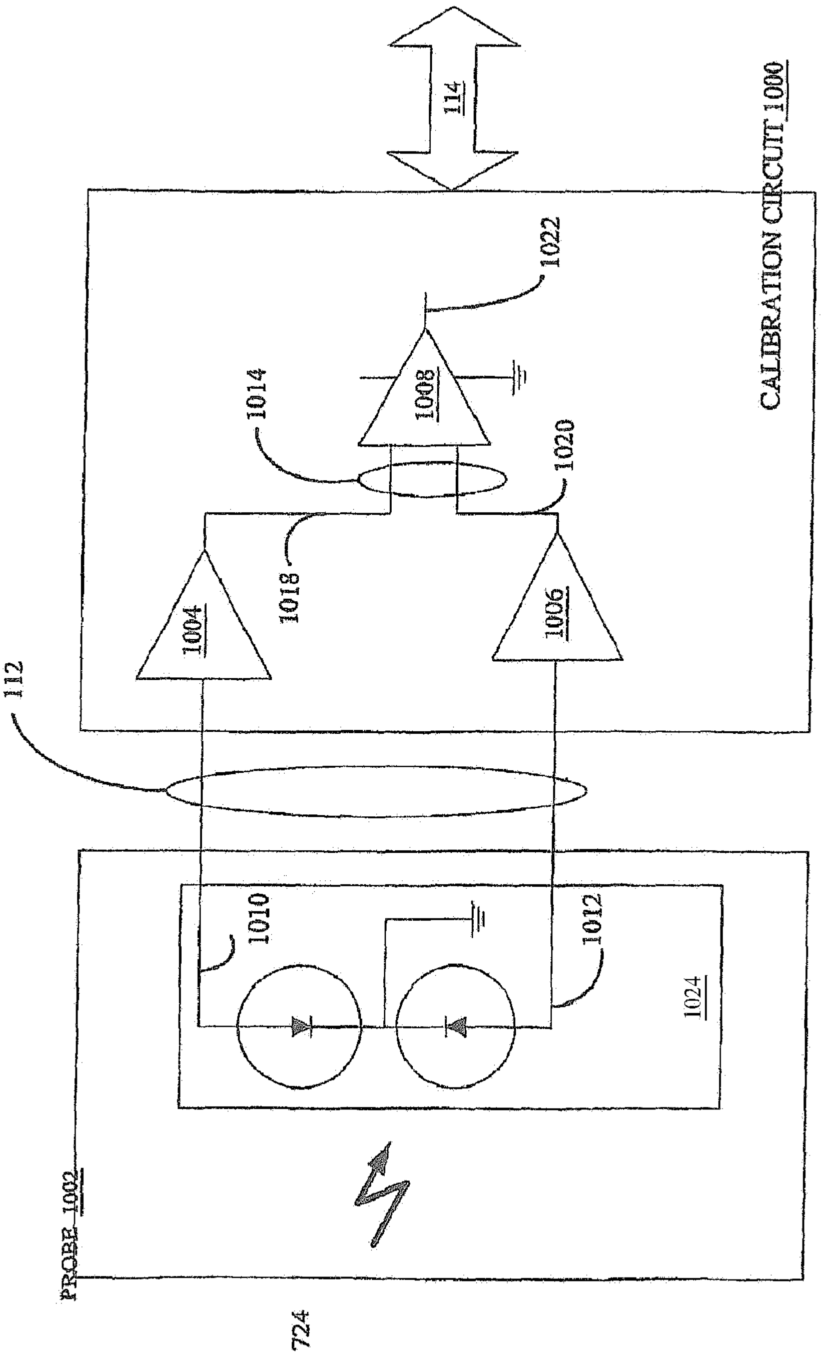
FIG. 10 is schematic diagram depicting an exemplary implementation of the calibration circuit block shown in FIG. 1.

In FIG. 10, a schematic diagram depicting an exemplary implementation of the calibration circuit 1000 is shown. The calibration circuit 1000 is in signal communication with the probe 1002 and controller 106, FIG. 1, via signal paths 112 and 114, respectively. The calibration circuit 1000 may include a pair of amplifiers 1004 and 1006 (such as log amplifiers) in signal communication with first anode 800, FIG. 8 and second anode 808 of wavelength sensor 1024, FIG. 10, and a differential amplifier 1008, via signal paths 1010, 1012, and 1014 respectively. The differential amplifier 1008 is in signal communication with the controller 106, FIG. 1, via signal path 112.

In operation, the wavelength sensor 1024 produces two photocurrent signals from the two junctions (i.e., photodiodes 804 and 806) the double diffusion photodiode, Each junction in the wavelength sensor 1024 exhibits a different and well-defined spectral response, which is know to the controller 106. FIG. 1, and the magnitude of these two resulting photocurrent signals are proportional to the wavelength of the measured incident light radiation 724, which corresponds to one of the light sources (either 204 or 206, FIG. 2) in probe 1002, FIG. 10. The photocurrent signals are amplified by amplifiers 1004 and 1006 via signal paths 1010 and 1012, respectively, and input into the differential amplifier 1008 via signal path 1018 and 1020. If the amplified photocurrent signals 1018 and 1020 are approximately equal the corresponding differential output signal 1022 of the differential amplifier 1008 is almost equal to zero. Once the differential output signal 1022 is almost equal to zero the wavelength of the incident light radiation is determined and the SCSS 100, FIG. 1, is calibrated.

When the amplified photocurrent signals 1018 and 1020 are not approximately equal the corresponding differential output signal 1022 will vary according to the difference in magnitude value between the amplified photocurrent signals 1018 and 1020. The differential output signal 1022 is the utilized as a reference by the controller 106, FIG. 1. The controller 106 determines the wavelength of the incident light radiation 724 by knowing the spectral response of the photodiodes 804 and 806, FIG. 8. The controller 106 either determines the wavelength of the incident light radiation 724 utilizing software 1008 or other hardware (not shown) located in the SCSS 100. The software 108 may include logic that allows the controller 106 to calculate the wavelength values in real-time from the measure values received from the wavelength sensor 1004.

Alternatively, the controller 106 may determine the wavelength of the incident light radiation 724 utilizing the lookup ("LUT") table 110. The LUT 110 may be resident in memory (not shown) resident either internally or externally to the controller 106. The LUT 110 includes a tabulation of known spectral response in voltage versus wavelength for each photodiode 804 and 806, FIG. 8. Once the controller 106 measures the differential output signal 1022, FIG. 10, the software 108, FIG. 1, compares the value of the differential output signal 1022, FIG. 10, against values stored in the LUT 110, FIG. 1, and then retrieves a corresponding wavelength value. The controller 106 then utilizes the retrieved wavelength wave to self-calibrate the SCSS 100.

Besides self-calibration, the SCSS 100 is also capable of temperature compensating for variation the wavelength of the incident light radiation 724 due to temperature variations. The SCSS 100 may compensate for temperature variations by the same process utilized to self-calibrate.

Figure 11:
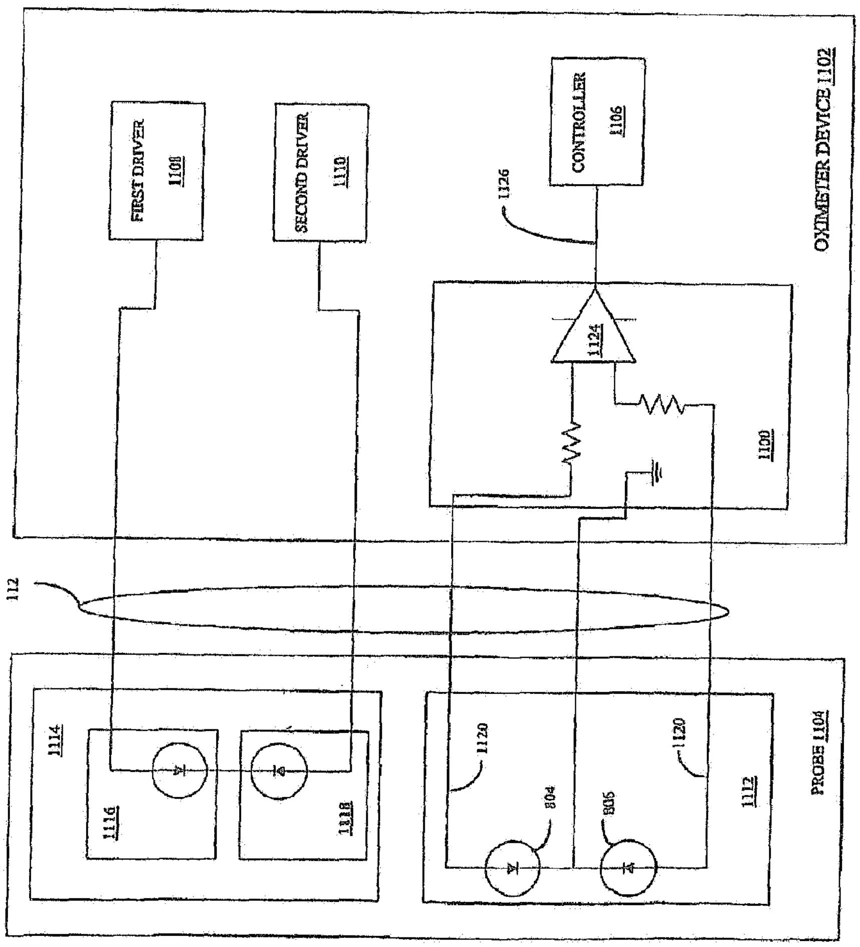
FIG. 11 is schematic diagram depicting another exemplary implementation of the calibration circuit block shown in FIG. 1.

FIG. 11 is another exemplary implementation of the SCSS 100, FIG. 1, with the calibration circuit 1100, FIG. 1, an oximeter device 1102. The oximeter device 1102 is in signal communication with probe 1104, via signal path 112, and includes calibration circuit 1100, controller 1106, first driver 1108 and second driver 1110, The probe 1104 includes wavelength sensor 1112 and probe light source 1114 having first light source 1116 and second light source 1118.

In operation, the first driver 1108 drives the first light source 1116 and the second driver 1110 drives the second light source 1118. First light source 1116 and the second light source 1118 may individually produce light radiation which is incident of the wavelength sensor 1112. The wavelength sensor 1112 produces two photocurrent signals from the two junctions (i.e., photodiodes 804 and 806) in the double diffusion photodiode. Again, each junction in the wavelength sensor 1112 exhibits a different and well-defined spectral response, which is know to the controller 1106 and the magnitude of these two resulting photocurrent signals are proportional to the wavelength of the measured incident light radiation, which corresponds to one of the light sources (either 1116 or 1118) in probe 1104. The photocurrent signals 1120 and 1122 processed and input into the differential amplifier 1224. If the photocurrent signals 1120 and 1122 are approximately equal the corresponding differential output signal 1126 of the differential amplifier 1124 is almost equal to zero. Once the differential output signal 1126 is almost equal to zero the wavelength of the incident light radiation is determined and the SCSS 100, FIG. 1, is calibrated.

When the photocurrent signals 1120 and 1122 are not approximately equal the corresponding differential output signal 1126 will vary according to the difference in magnitude value between the photocurrent signals 1120 and 1122. The differential output signal 1126 is the utilized as reference by the controller 1106. The controller 1106 determines the wavelength of be incident light radiation by knowing the spectral response of the photodiodes 804 and 806.

The controller 1106 either determines the wavelength of the incident light radiation utilizing software 108, FIG. 1, or other hardware (not shown) located in the SCSS 100. The software 108 may include logic that allows controller 1106, FIG. 11, to calculate the wavelength values in real-time from the measure values received from the wavelength sensor 1112.

Alternatively, the controller 1106 may determine the wavelength of the incident light radiation utilizing the lookup LUT 110, FIG. 1. The LUT 110 may be resident in memory (not shown) resident either internally or externally to the controller 1106, FIG. 11. The LUT 110, FIG. 1, includes the tabulation of known spectral response in voltage versus wavelength for each photodiode 804 and 806. Once the controller 1106 measures the differential output signal 1126, FIG. 11, the software 108, FIG. 1, compares the value of the differential output signal 1126, FIG. 11, against values stored in the LUT 110, FIG. 1, and then retrieves a corresponding wavelength value. The controller 1106, FIG. 11, then utilizes the retrieved wavelength wave to self-calibrate the SCSS 100, FIG. 1.

Figure 12:
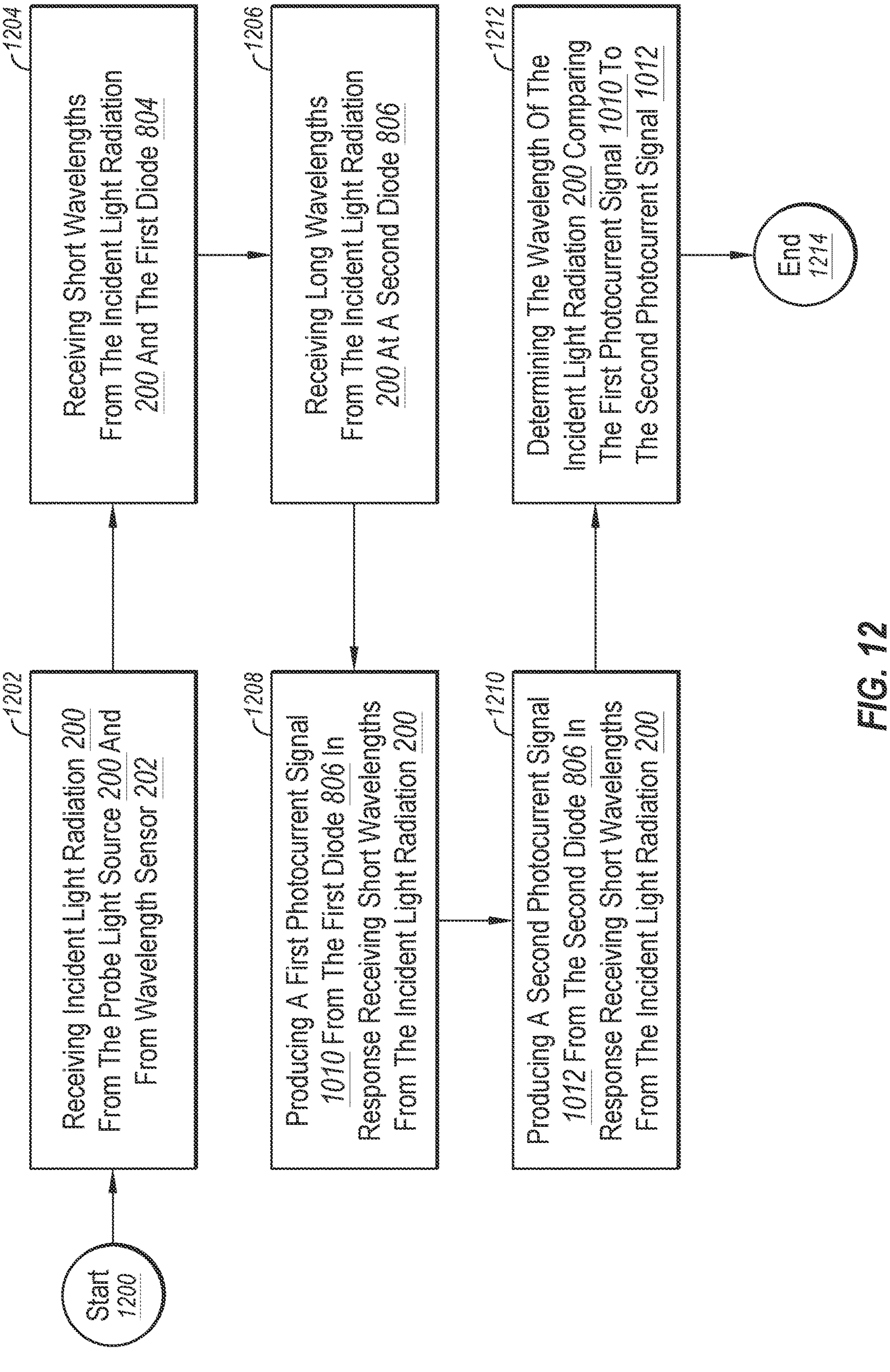
FIG. 12 is a flow chart illustrating the process performed by the SCSS shown in FIG. 1.

FIG. 12 illustrates the process performed by the SCSS 100. FIG. 1. The process begins in step 1200, FIG. 12. In step 1202, the wavelength sensor 202, FIG. 2, receives incident light radiation 200 from the probe light source 200. Within the wavelength sensor 202, the first diode 804, FIG. 8, receives short wavelengths from the incident light radiation 200, in step 1204, FIG. 12, and the second diode 806, FIG. 8, receives long wavelengths from the incident light radiation 200 in step 1206, FIG. 12. In step 1208, the first diode 804 produces a first photocurrent signal 1010, FIG. 10, in response to receiving short wavelengths from the incident light radiation 200 and the second diode 806 produces a second photocurrent signal 1012, FIG. 10, in response to receiving short wavelengths from the incident light radiation 200 in step 1210, FIG. 12. Finally, in step 1212, the calibration circuit 104 and/or controller 106, FIG. 1, determine the wavelength of the incident light radiation 200 by comparing the first photocurrent signal 1010 to the second photocurrent signal 1012. The process then ends in step 1214.

The SCSS 100 may be selectively implemented in software, hardware, or a combination of hardware and software. For example, the elements of the SCSS 100 may be implemented in software 108 stored in a memory (not shown) located in a controller 106. The controller 106 may in signal communication with a DSP or ASIC chip via communication link 112 (which may selectively be a system bus). The software 108 configures and drives the DSP or ASIC chip and performs the steps illustrated in FIG. 12.

The software 108 comprises an ordered listing of executable instructions for implementing logical functions. The software 108 may embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this document, a "computer-readable medium" is any means that may contain, store, communicate, propagate, or transport the program for use by or in connection with the instruction execution system, apparatus, or device. The computer readable medium may be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a RAM (electronic), a read-only memory (ROM) (electronic), an erasable programmable read-only memory (EPROM or Flash memory) (electronic), an optical fiber (optical), and a portable compact disc read-only memory (CDROM) (optical), Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Figure 13:
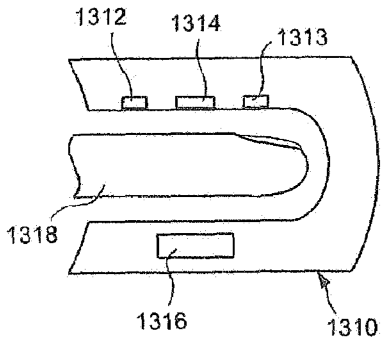
FIG. 13 is a simplified cross-sectional view of a sensor in accordance with the present invention.

Turning to FIG. 13, in an embodiment, a non-invasive medical sensor is provided for detecting blood constituents of any kind. For instance, the sensor 1310 can be for detecting oxygen saturation of hemoglobin or other parameters.

The sensor 1310 can, but not necessarily, have one or more monochromatic light sources 1312, 1313, one or more broadband, non-monochromatic light source 1314 and one or more light detectors 1316. In an embodiment, the light sources and the detectors are mounted oppose to each other as shown in FIG. 13.

Figure 14:
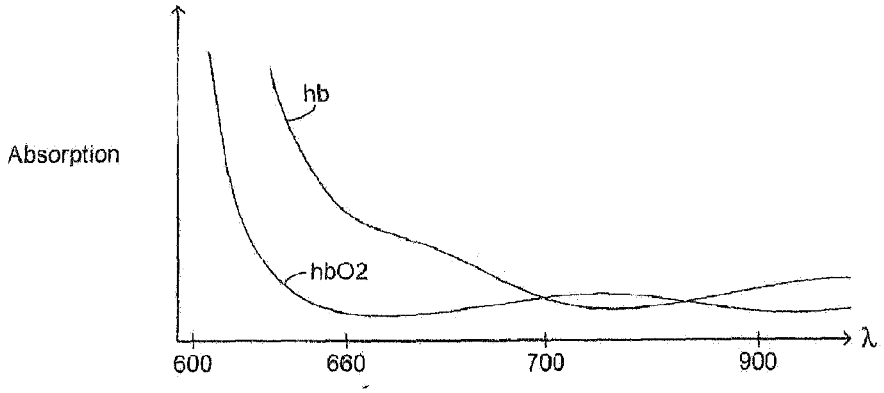
FIG. 14 is a chart depicting the typical spectral absorption characteristics of an arterial and venous pulse.

In an embodiment, the sensor 1310 is placed on a finger 1318 or other extremity of the human body and shines light from the one or more light sources through the extremity. FIG. 14 provides a depiction of a typical spectral transmission of both oxygenated (arterial) hbO2 and deoxygenated (venous) hb haemoglobin molecules (hg). Alternatively, the light is reflected off the skin of a part of the human body, instead of being shined through the extremity.

Figure 15:
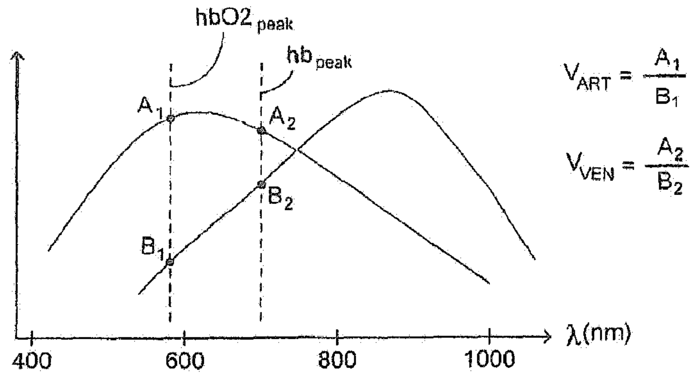
FIG. 15 is a chart depicting response of the wavelength sensor to both arterial and venous pulses.

As indicated previously, the sensor 1310 includes a wavelength detector 1316, such as a dual photodiode or any other type, which produces an output indicating the centroid wavelength of the received light. FIG. 15 depicts responsiveness of a dual junction wavelength detector for both hbO2 (arterial) and hb (venous) blood flow using a broad spectrum light source.

Figure 16:
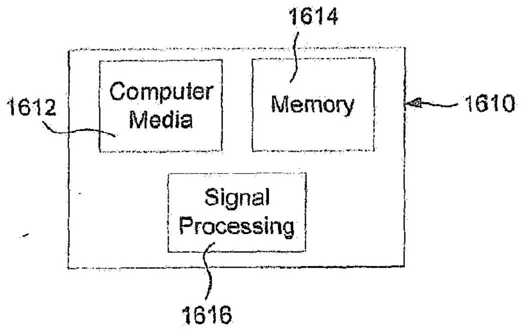
FIG. 16 is a simplified block diagram of a processing system foe use with the sensor of FIG. 13.

The sensor 1310 can further include a tight source that emits light of a wide light spectrum from, for instance, 200 nm to 2000 nm or any portion thereof, such as a white LED or any other broad emission device. The sensor 1310 can be connected to a processing system 1610 (FIG. 16) that drives the light sources, including the broad emission device, and also receives signals from the photodiodes and the wavelength detector.

In an embodiment, the processing system 1610 contains, among other things, computer media 1612, memory 1614, and signal processing circuitry 1616 used to calculate various parameters of the blood stream through comparison of the signals received by the photodiodes of the sensor 1310. Moreover, the processing system 1610 can be used to illuminate the tissue with light generated from the broad emission light source within the sensor.

Figure 17:
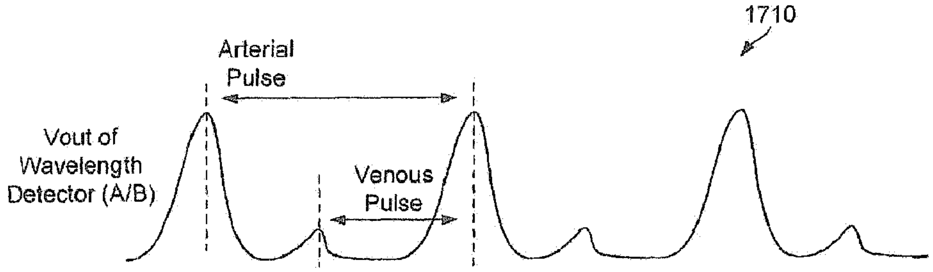
FIG. 17 is a chart depicting a pulse waveform proportional to the arterial and venous pulse of the human body as produced after processing the signals from the wavelength sensor.

Moreover, in an embodiment, the wavelength detector 1316 generates a signal proportional to the strongest transmission wavelength of the light emitted from the broad emission light source 1314 after the light either passes through the body part 1318 or is reflected from the skin of a human. Turning to FIG. 17, a signal derived from the wavelength detector 1316 can be further processed by circuitry and computer processing, via the processing system 1610, to obtain a pulse waveform 1710 proportional to the arterial and venous pulse of the human body.

Via the processing system 1610, the time domain and amplitude properties of both arterial and venous pulse can be stored and further used to synchronize an arterial-pulse synchronized measurement of the absorption or reflectance of one or more monochromatic light-sources 1312,1313 through the body's extremity 1318. These signals can then be used in calculating oxygen saturation, carbon-monoxide concentration, haemoglobin or any other parameter of the blood.

In an embodiment, the arterial and venous pulse coinciding wavelength detector signals can be used to eliminate or reduce false pulses commonly caused by motion of the human body or extremity, commonly labeled motion artifact, that could cause erroneous measurements.

Utilizing the non-invasive sensor shown in FIG. 13 may allow for the system to intake additional measurements and calculations as well.

As discussed herein, the sensor may contain at least one monochromatic light source, at least one non-monochromatic broad spectrum emission light source, at least one light detector, and at least one wavelength detector. The light sources and detectors may be mounted opposing each other, or may be mounted adjacent each other. The sensor may be placed on tissue like a finger (as shown in FIG. 13) or other extremity, or any other positon that provides sufficient blood perfusion for measurement for measurement. When the tight sources are mounted opposite the detectors, perfusion may result from emitted light passing through the finger or other body part. When mounted adjacent, the emitted light may be reflected off the skin or other body part, which may provide adequate blood perfusion for measurement.

Figure 18:
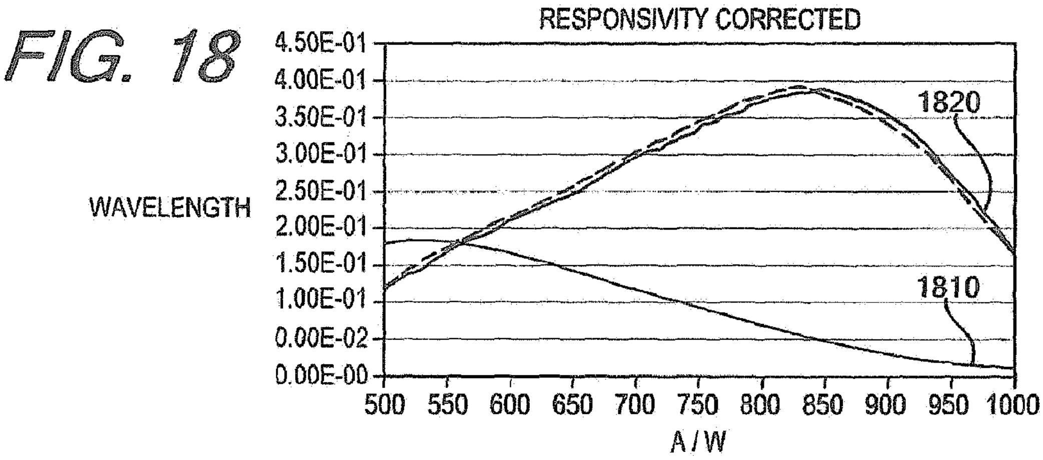
FIG. 18 is a chart depicting the response curves of the detectors of a dual detector module contemplated by the invention.

As already described herein, the detector module may be a dual element light receiver or a dual junction detector element. The dual detector module utilized in the system may, for example, include two photodiodes (detector A and detector B) with different and tightly controlled spectral response curves. The photodiodes may be constructed, for example, on a single chip epitaxial silicon die. The system relies on the characteristics of the detector module to derive a signal proportional to the centroid wavelength of impinging light. A typical response curve of the detector can be seen, for example, in FIG. 18 where curve 1810 shows the responsive curve of detector A, while curve 1820 shows the response curve of detector B.

The sensor and system may include at least one or more light sources which emit non-monochromatic light energy of a broad spectrum, like for example, a white LED, The broad spectrum may cover the range of 200 nm to 1300 nm or any portion thereof. The sensor and system may further include one or more monochromatic light elements. For example, the sensor and system may include a red LED and an IR emitter which emit light to be received by the detector module through or across an extremity or tissue.

The sensor may be connected to a processing system which drives the light sources in a sequential, pulsed mode. The processing system may receive signals from the light receiver elements and the centroid wavelength detector. The processing system may include computer media, memory, and signal processing circuitry which is used to process the signals derived from light detectors contained in the sensor and derive various physiological parameters from these signals. The processing system may also provide control signals to the sensor. The signals may be used to illuminate the light sources which in turn illuminate the tissue or extremity in contact with the sensor. Illumination may occur from the at least one monochromatic light source as well as any one non-monochromatic light sources.

The photodiodes and centroid wavelength detector module may generate a signal proportional to the highest light intensity wavelength as filtered and either passed through an extremity or tissue, or reflected through the skin or tissue. The signal may be further processed to determine modulation in the signal proportional to the arterial pulse and spectral absorption changes between the peak and trough of the arterial pulse. The signal received from the sensor may be further used to correlate changes in spectral absorption to the pulse by pulse blood oxygen concentration as well as other blood constituents.

Figure 19:
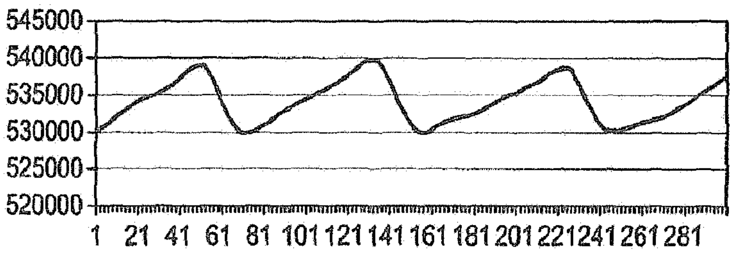
FIG. 19 is a chart depicting the change in spectral absorption generated by the arterial pulse blood flow with a broad emission illumination emitter as detected by a centroid wavelength detector as contemplated by the invention.
Figure 20:
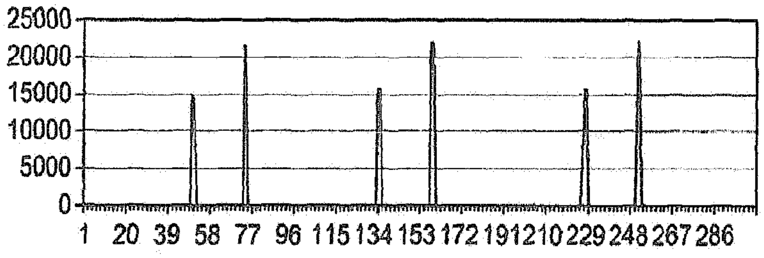
FIG. 20 is a chart depicting the peak and valley of the spectral absorption in the time domain.

FIG. 19 represents the change in spectral absorption generated by the arterial pulse blood flow with a broad emission illumination emitter as detected by a centroid wavelength detector and processed by the system described herein. FIG. 20 depicts the peak and valley of such signal in the tune domain, the valley coinciding with the peak of the arterial pulse of a patient.

Figure 21:
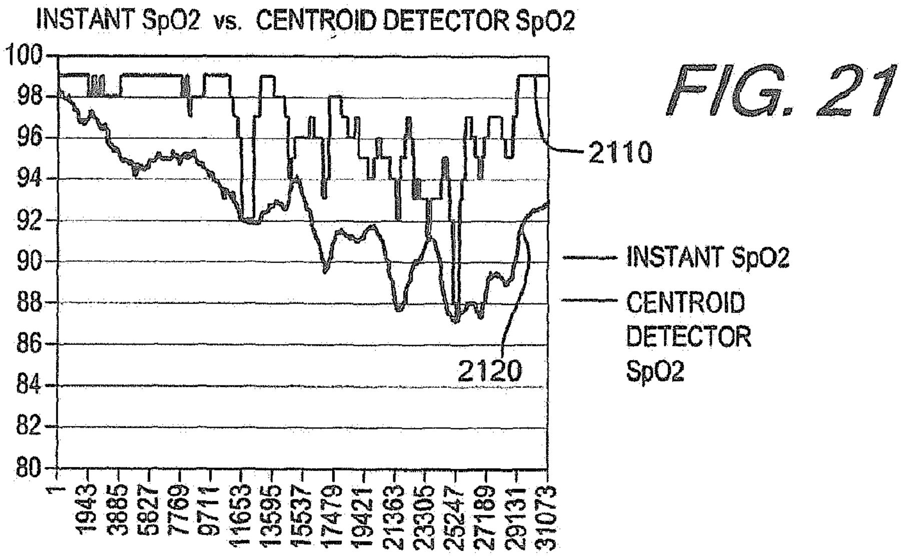
FIG. 21 is a chart which depicts a signal proportional to the blood oxygen saturation level.

The benefit to using the present system and method for determining blood oxygenation, for example, can be seen in FIG. 21 which shows the signal proportional to blood oxygen saturation derived and processed from centroid wavelength detector ratios (2110) and the pulse by pulse blood oxygen saturation derived from monochromatic light sources used in traditional oximeters (2120). As seen in FIG. 21, utilizing the centroid wavelength detector ratios provides a reasonably accurate and dynamically updated oxygen saturation measurement.

Utilizing the pulse blood oxygen saturation data from the non-monochromatic light element, a reliable data stream for blood oxygen concentrations or other blood constituent parameters during motion events occurring at the sensor site may be obtained and calculated. Events that normally would mask or invalidate data derived from only monochromatic illumination of tissue can be corrected or replaced. The substitute data derived from the changes in spectral absorption of the non-monochromatic illuminated tissue derived from a sensor for data normally derived from monochromatic light sources such as found in traditional pulse-oximeter systems may be used to correct or replace inaccurate data from the traditional monochromatic light sources.

Figure 22A:
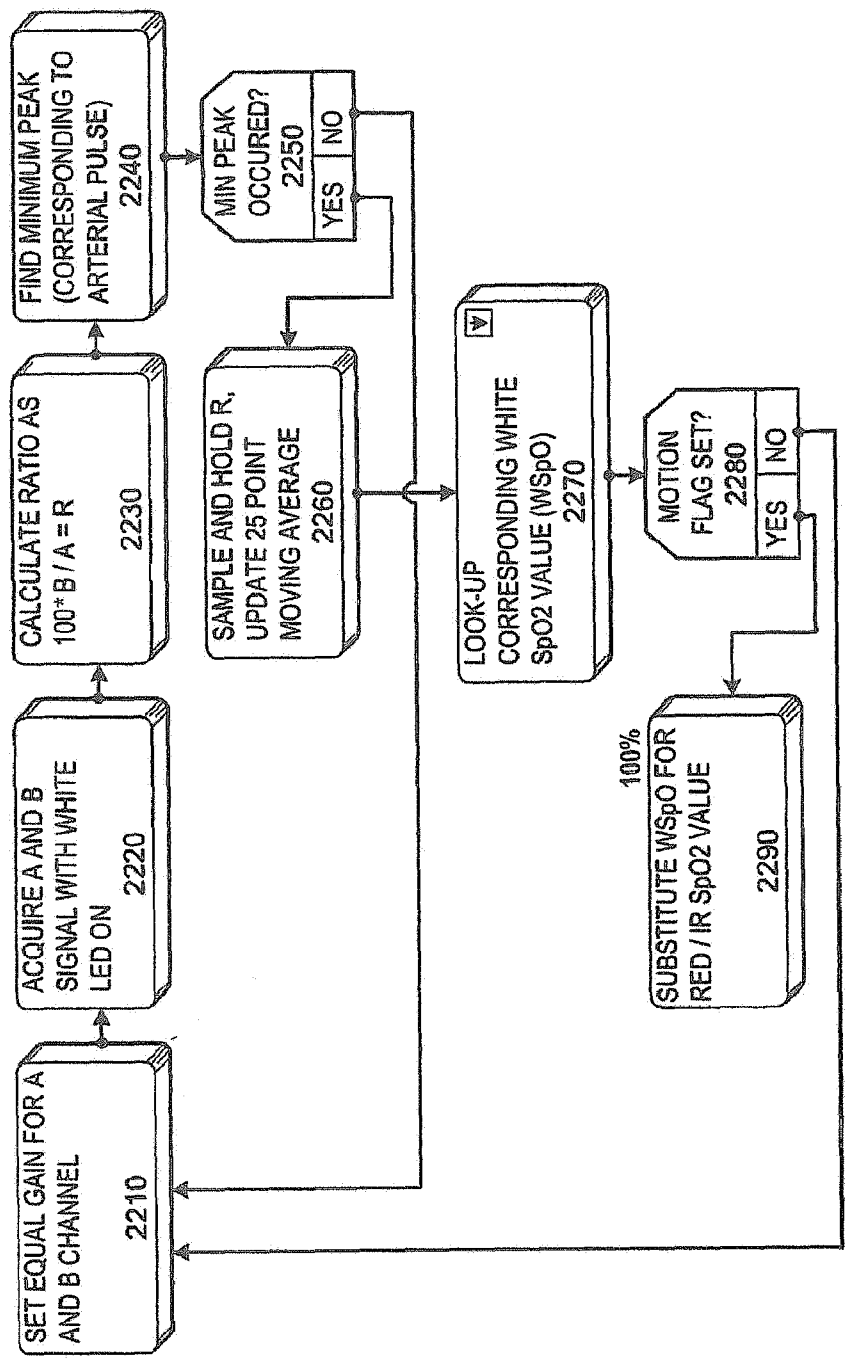
FIG. 22A is a flow chart showing the process through which pulse detection may be read and provided the system through a motion event.
Figures 22B, 23:
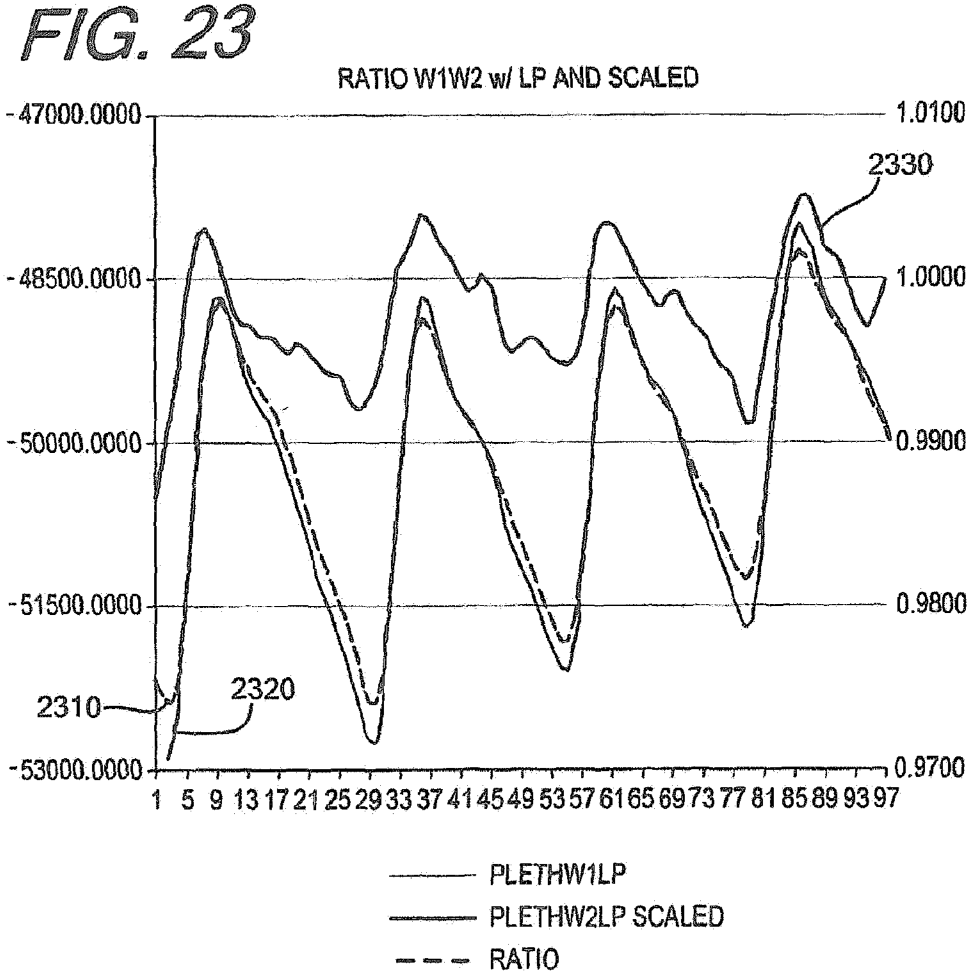
FIG. 22B shows an exemplary look up table utilized in the process shown in FIG. 22A.
FIG. 23 is a chart depicting saturation levels of a patient at rest.
Figure 24:
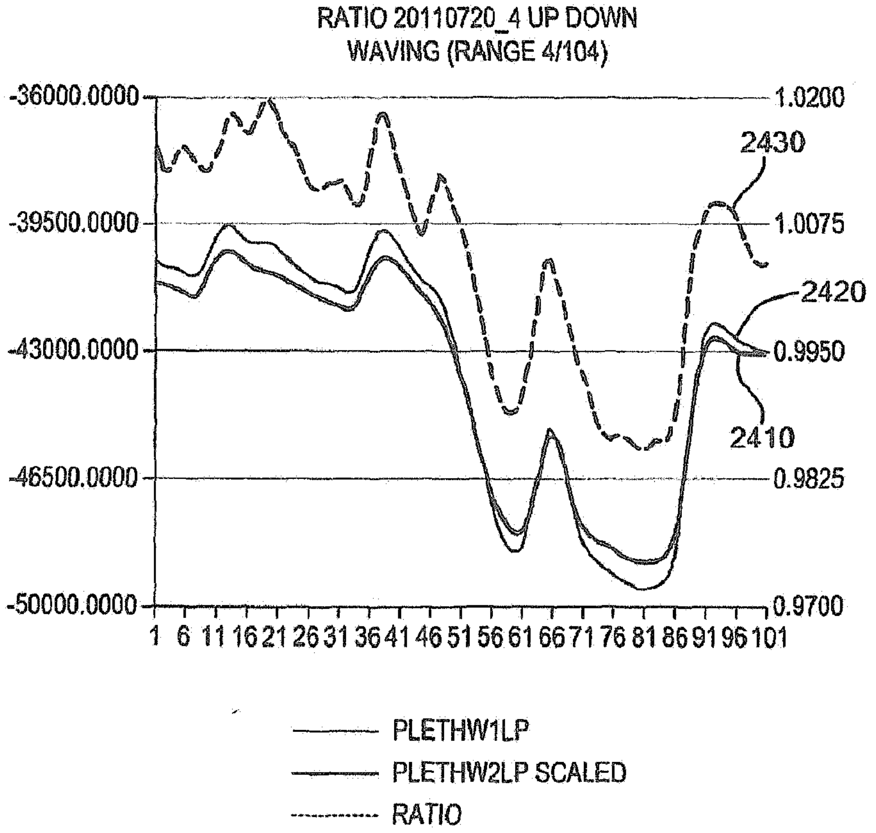
FIG. 24 is a chart depicting saturation levels detected during a motion event.

FIGS. 22-24 show the process by pulse detection may be read and provided through a motion event occurring with the patient. The non-monochromatic broad spectrum light emitting element may be illuminated and the emitted light pass through a patient's tissue before being detected and received by the dual detector element. The arterial pulse will change the spectral absorption enough to allow the system to detect the pulse occurring. After an equal gain is set for detectors A and B (2210), the needed analogue data generated by turning on the broad spectrum element periodically, like for example 30 times per second for a brief duration and sampling of the signals at both detector A and detector B at the same gain (2220). The ratio of these two signals may be calculated (2230) and a result in a generated signal that reflects the average and changes in spectral absorption generated by both the occurrence of the arterial pulse and base line spectral absorption of the tissue. The system will then find the minimum peak signal which corresponds to the arterial pulse (2240) and determine whether or not the minimum peak occurred (2250). If the minimum peak did not occur, the system will reset the equal gain for detectors A and B and resample and recalculate the ratio.

If the minimum peak has occurred, it will sample and hold the ratio (2260). Using the sampled and held Rs, an average ratio of the previous 25 samplings will be continuously updated to create a moving point average. The system will then take the ratio and look up the corresponding SpO2 value from a stored table (2270), shown in FIG. 22B, and determine if a motion flag should has been set (2280). If the currently measured ratio is within the acceptable range in the system, the process will repeat for the next sample. If the measured ratio is not within the acceptable range in the system, the system will substitute the SpO2 value obtained based on the non-monochromatic LED for any monochromatic Red/IR SpO2 value (2290).

The ratio signal is used to establish a fall-back data stream in the event of a motion event occurring that makes it impossible to accurately calculate the oxygen saturation from the AC component ratio of red LED and IR emitter. During normal operation the oxygen saturation data from red to IR ratio needs to be correlated to a corresponding value (preferably sampled at the arterial peak) of signal level derived from the ratio of the two elements while the broad spectrum light source is on. If a motion even occurs, the system will revert back to that broad spectrum light source derived data stream to generate accurate oxygen saturation data during the motion event by substituting that data for the saturation data normally calculated from the red to IR ratio. For this reason, the non-monochromatic broad spectrum light source must be turned on in sequence every time the red LED and IR emitter are activated.

The plot typically derived from tissue illuminated by the non-monochromatic or white LED or\n a patient at rest and normal saturation levels can be seen in FIG. 23, where curve 2310 shows the pleth of detector A and curve 2320 shows the pleth of detector B. The "Ratio" of detected light by photodiode A and photodiode B is also calculated as seen by ratio curve 2330. FIG. 24 shows the acquired pleth and A/B ratio during a rapid extremity wave or movement motion event on a normally saturated extremity. As seen in FIG. 24, the excursions of the pleth amplitude, which a traditional oximeter relies on, are in excess of 21%, the A/B ratio which represents only spectral absorption, changes only 1.5.

The system may also be configured to measure the centroid wavelength of light produced by the non-monochromatic light source. Measuring the centroid wavelength allows for the system to detect when a probe or device is operating outside a centroid wavelength range in order to insure accuracy. The measurement may occur while the probe is applied to the patient and when the red light source, is energized. The centroid wavelength data may be collected periodically, like for example every five (5) seconds or every 150 pulses based on an emitter pulse rate of 30 per second. The centroid data may be calculated by sampling both detector A and B in the dual detector element while the red LED is energized. The ratio of A to B corresponds to the centroid wavelength of the light emitted by the red LED and can be compared to limits embedded in the system and compared to acceptable values that assure accurate saturation measurements. It is not necessary to collect data for the IR emitter as the centroid wavelength of the IR emitter does not have a direct bearing on the accuracy of the saturation calculation. Since the measurement is taken on the patient, the system will detect shifts in the centroid wavelength induced by, for example, substances on the patient's extremity or skin pigmentation, skin defects, or the like. A system message can be generated if the centroid fails outside the limits within the system, alerting the user to replace the probe as readings may be inaccurate. Such readings may result from a motion event, as discussed above, or may be the result of the sensor becoming disengaged from the patient.

Figure 25:
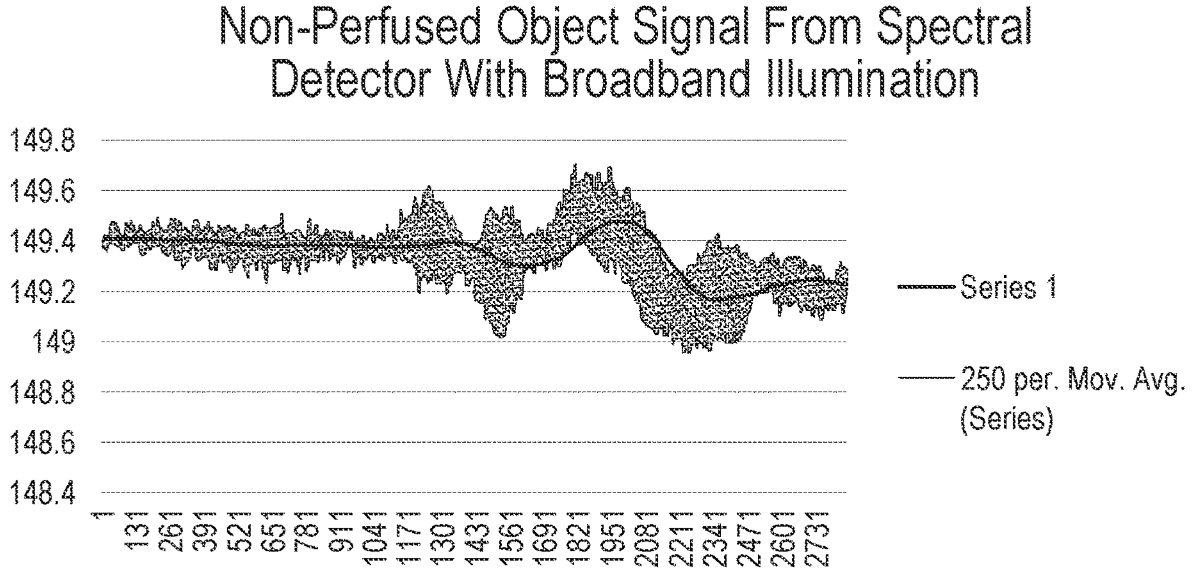
FIG. 25 is a chart depicting raw data provided by a wavelength detector resulting from a non-perfused signal.
Figure 26:
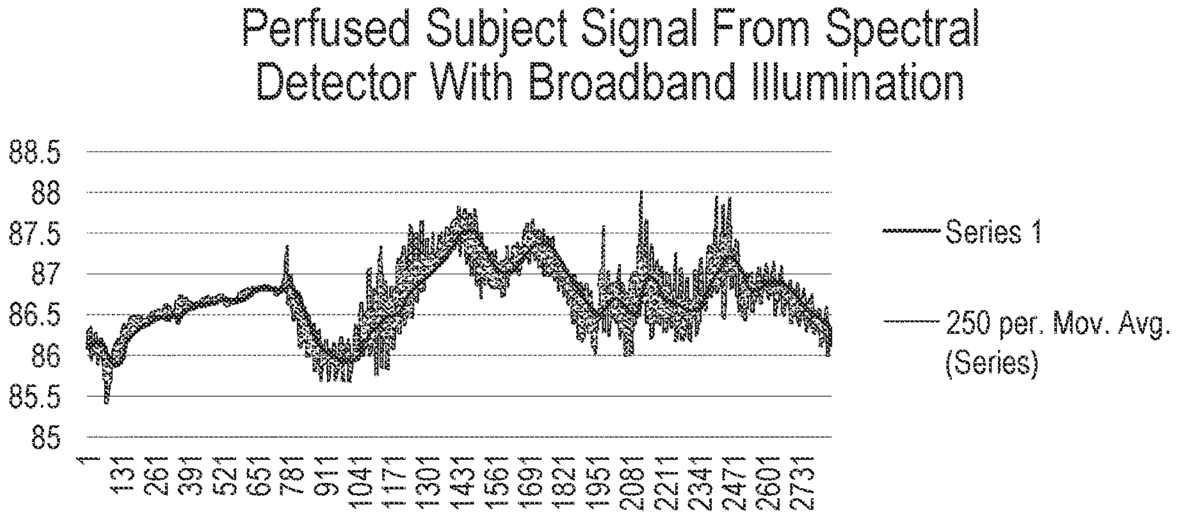
FIG. 26 is a chart depicting raw data provided by a wavelength detector resulting from a perfused signal.

FIGS. 25 and 26 show raw data provided from the wavelength detector using non-monochromatic broad-band (white) source and non-perfused object and a perfused object. Ratio based amplitudes of 110 or higher indicate a non-perfused object, while amplitudes of 90 or lower indicate the presence of a perfused subject. By setting limits and detecting the raw data in the wavelength detector, the detector can accurately determine whether or not an extremity or tissue is located within the sensor, and whether or not the light is passing through the tissue or being directly provided to the sensor.

While various implementations of the application have been described, it will be apparent to those of ordinary skill in the art that many more embodiments and implementations are possible that are within the scope of the invention. Accordingly, the invention is not to be restricted except in light of the attached claims and their equivalents.

What is claimed is:

1. A method, comprising:

providing a first detector and a second detector in a non-invasive optical sensor, the first detector and the second detector having differing spectral responses across a wavelength range of about 450 nm to about 900 nm;

emitting light from a non-monochromatic light source in the non-invasive optical sensor;

detecting with each of the first detector and the second detector non-monochromatic light emitted from the non-monochromatic light source;

generating an oxygen saturation value based on the non-monochromatic light detected by each of the first and second detectors;

wherein detecting with the first detector and the second detector non-monochromatic light emitted from the non-monochromatic light source includes providing a ratio between signals corresponding to light detected by the first detector and light detected second signal of the second detector; and wherein generating the oxygen saturation value includes determining an oxygen saturation value corresponding to the ratio.

2. The method of claim 1, further comprising passing the light emitted from the non-monochromatic light source through tissue before detecting with the first detector and the second detector.

3. The method of claim 1, wherein the ratio reflects average and changes in spectral absorption generated by arterial pulse and baseline spectral absorption of tissue.

4. The method of claim 1, wherein the non-monochromatic light source is configured to produce non-monochromatic light having a wavelength in the range of about 200 nm to about 2000 nm.

5. The method of claim 4, wherein the non-monochromatic light source is configured to produce non-monochromatic light having a wavelength in the range of about 200 nm to about 1300 nm.

6. The method of claim 1, where the first detector and the second detector are photodiodes.

7. The method of claim 6, wherein the photodiodes are constructed on a single chip epitaxial silicon die.

8. A method, comprising:

providing a first detector and a second detector in a non-invasive optical sensor, the first detector and the second detector having differing spectral responses across a wavelength range of 450 nm to about 900 nm;

emitting light from a non-monochromatic light source in the non-invasive optical sensor;

detecting with each of the first detector and the second detector non-monochromatic light emitted from the non-monochromatic light source;

generating an oxygen saturation value based on the non-monochromatic light detected by each of the first and second detectors; and determining an average ratio value between the signals for a plurality of detections by the first detector and the second detector.

9. The method of claim 8, wherein generating the oxygen saturation value includes determining an oxygen saturation value corresponding to the average ratio.

10. A system, comprising:

a non-monochromatic light source configured to provide non-monochromatic light;

a wavelength sensor including a first detector with a first spectral response and a second detector with a second spectral response different from the first spectral response, the first detector and the second detector each being configured to detect non-monochromatic light from the non-monochromatic light source, and the first spectral response and the second spectral response each covering a spectral range of at least about 450 nm to about 900 nm; and a processor configured to:

generate a first signal from the first detector and a second signal from the second detector resulting from non-monochromatic light periodically emitted by the non-monochromatic light source sampled by the first detector and the second detector; and generate an oxygen saturation value based on a ratio between first signal and the second signal.

11. The system of claim 10, wherein the first detector and the second detector are photodiodes.

12. The system of claim 11, wherein the photodiodes are constructed on a single chip epitaxial silicon die.

13. The system of claim 10, wherein the processor is further configured to generate the oxygen saturation value based on an average ratio of the first signal and the second signal corresponding to a plurality of detections by the first detector and the second detector.

14. The system of claim 10, wherein the non-monochromatic light source is configured to produce non-monochromatic light having a wavelength in the range of about 200 nm to about 2000 nm.

15. The system of claim 10, wherein the non-monochromatic light source is configured to produce non-monochromatic light having a wavelength in the range of about 200 nm to about 1300 nm.

16. The system of claim 10, wherein the ratio reflects average and changes in spectral absorption generated by arterial pulse and baseline spectral absorption of tissue.

17. The system of claim 10, wherein the non-monochromatic light source is configured to produce non-monochromatic light having a wavelength in the range of about 200 nm to about 400 nm.

18. The system of claim 10, wherein the non-monochromatic light source is configured to produce non-monochromatic light having a wavelength in the range of about 1000 nm to about 1500 nm.

* * * * *